United States Patent [19]

Masferrer et al.

[11] Patent Number: 6,025,353
[45] Date of Patent: Feb. 15, 2000

[54] METHOD OF USING CYCLOOXYGENASE-2 INHIBITORS AS ANTI-ANGIOGENIC AGENTS

[75] Inventors: Jaime Masferrer, Ballwin, Mo.; Amiram Raz, Ramat-Gan, Israel

[73] Assignee: G.D. Searle & Co., Skokie, Ill.

[21] Appl. No.: 08/974,201

[22] Filed: Nov. 19, 1997

[51] Int. Cl.$^7$ .................................................. A61K 43/56
[52] U.S. Cl. .......................... 514/210; 514/341; 514/365; 514/372; 514/374; 514/378; 514/399; 514/400; 514/403; 514/406; 514/407
[58] Field of Search .................................. 514/210, 341, 514/365, 372, 374, 378, 399, 400, 403, 406, 407

[56] References Cited

U.S. PATENT DOCUMENTS

| | | | |
|---|---|---|---|
| 5,344,991 | 9/1994 | Reitz et al. | 568/34 |
| 5,380,738 | 1/1995 | Norman et al. | 514/374 |
| 5,393,790 | 2/1995 | Reitz et al. | 514/709 |
| 5,434,178 | 7/1995 | Talley et al. | 514/406 |
| 5,466,823 | 11/1995 | Talley et al. | 548/377.1 |
| 5,474,995 | 12/1995 | Ducharme et al. | 514/241 |
| 5,475,018 | 12/1995 | Lee et al. | 514/406 |
| 5,510,368 | 4/1996 | Lau et al. | 514/419 |
| 5,521,207 | 5/1996 | Graneto | 514/406 |
| 5,646,136 | 7/1997 | Petrow et al. | 514/167 |
| 5,760,068 | 6/1998 | Talley et al. | 514/403 |

FOREIGN PATENT DOCUMENTS

| | | |
|---|---|---|
| 2 283 745 | 5/1995 | United Kingdom . |
| WO94/13635 A1 | 6/1994 | WIPO . |
| WO94/15932 A1 | 7/1994 | WIPO . |
| WO94/20480 A1 | 9/1994 | WIPO . |
| WO94/26731 A1 | 11/1994 | WIPO . |
| WO94/27980 A1 | 12/1994 | WIPO . |
| WO95/00501 A2 | 1/1995 | WIPO . |
| WO95/15316 A1 | 6/1995 | WIPO . |
| WO95/21817 A1 | 8/1995 | WIPO . |
| WO96/03385 A1 | 2/1996 | WIPO . |
| WO96/03387 A1 | 2/1996 | WIPO . |
| WO96/03388 A1 | 2/1996 | WIPO . |
| WO96/03392 A1 | 2/1996 | WIPO . |
| WO96/06840 A1 | 3/1996 | WIPO . |
| WO96/16934 A1 | 6/1996 | WIPO . |
| WO96/19469 A1 | 6/1996 | WIPO . |
| WO96/24584 A1 | 8/1996 | WIPO . |
| WO96/25405 A1 | 8/1996 | WIPO . |
| WO96/36623 A1 | 11/1996 | WIPO . |

OTHER PUBLICATIONS

Bouck, N. et al., "How Tumors Become Angiogenic", *Advances in Cancer Research*, vol. 69, pp. 136–173, 1996.

Ferrera, N. et al., "The Biology of Vascular Endothelial Growth Factor", *Endocrine Reviews*, vol. 18, No. 1, pp. 4–25, 1997.

Folkman, J., "Angiogenesis in Cancer, Vascular, Rheumatoid and Other Disease", *Nature Medicine*, vol. 1, No. 1, pp. 27–31, 1995.

Form, D.M. et al., "PGE$_2$ and Angiogenesis", *Proceedings of the Society for Experimental Biology and Medicine*, vol. 172, pp. 214–218, 1983.

Fujii, E. et al., "Role of Nitric Oxide, Prostaglandins and Tyrosine Kinase in Vascular Endothelial Growth Factor–Induced Increase in Vascular Permeability in Mouse Skin", *Naunyn–Schmiedeberg's Arch. Pharmacol.*, vol. 356, pp. 475–480, 1997.

Hamilton, J.A., "Hypothesis: In Vitro Evidence for the Invasive and Tumor–Like Properties of the Rheumatoid Pannus", *The Journal of Rheumatology*, vol. 10:6, pp. 845–851, 1983.

Heldin, C., "Structural and Functional Studies on Platelet-–Derived Growth Factor", *The EMBO Journal*, vol. 11, No. 12, pp. 4251–4259, 1992.

Hla, T. et al., "Role of the Early Response Gene Cyclooxygenase (Cox)–2 in Angiogenesis", *Molecular, Cellular, and Clinical Aspects of Angiogenesis*, pp. 191–198, 1996.

Huang et al., "Cyclooxygenase and 5–Lipoxygenase Inhibitors for the Prevention and Treatment of Cancer", *Expert Opinion on Investigational Drugs*, vol. 4(3), pp. 243–249, 1995.

Lala, P.K. et al., "Effects of Chronic Indomethacin Therapy on the Development and Progression of Spontaneous Mamary Tumors in C3H/HEJ Mice", *Int. J. Cancer*, vol. 73, pp. 371–380, 1997.

McGough, K.A. et al., "Inflammatory PGE$_2$ Production is Maintained During Hypoxia in Rheumatoid Synovial Fibroblasts", *Inflammation Research*, vol. 46, Supplement 2, pp. S147–S148, 1997.

Murohara, T. et al., "Vascular Endothelial Growth Factor/Vascular Permeability Factor Enhances Vascular Permeability Via Nitric Oxide and Prostacyclin", *Circulation*, vol. 97, pp. 99–107, 1998.

Nagashima, M. et al., "Role of Vascular Endothelial Growth Factor in Angiogenesis of Rheumatoid Arthritis", *The Journal of Rheumatology*, vol. 22, pp. 1624–1630, 1995.

Peterson, H., "Tumor Angiogenesis Inhibition by Prostaglandin Synthetase Inhibitors", *Anticancer Research*, vol. 6, pp. 251–254, 1986.

(List continued on next page.)

*Primary Examiner*—Frederick Krass
*Attorney, Agent, or Firm*—Joseph W. Bulock

[57] ABSTRACT

This invention relates to the use of cyclooxygenase-2 inhibitors or derivatives thereof in preventing and treating angiogenic disorders.

22 Claims, No Drawings

OTHER PUBLICATIONS

Ristimaki, A. et al., "Effect of Growth Factors on Human Vascular Endothelial Cell Prostacyclin Production", *Arteriosclerosis*, vol. 10, No. 4, pp. 653–657, 1990.

Sano, H. et al., "Expression of Cyclooxygenase–1 and –2 in Human Colorectal Cancer", *Cancer Research*, vol. 55, pp. 3785–3789, 1995.

Sano, H. et al., "In Vivo Cyclooxygenase Expression in Synovial Tissues of Patients With Rheumatoid Arthritis and Osteoarthritis and Rats With Adjuvant and Streptococcal Cell Wall Arthritis", *The Journal of Clinical Investigation, Inc.*, vol. 89, pp. 97–108, 1992.

Seed, M.P. et al., "The Inhibition of Colon–26 Adenocarcinoma Development and Angiogenesis by Topical Diclofenac in 2.5% Hyaluronan", *Cancer Research*, vol. 57, pp. 1625–1629, 1997.

Ziche, M. et al., "Nitric Oxide Mediates Angiogenesis In Vivo and Endothelial Cell Growth and Migration In Vitro Promoted by Substance P", *J. Clin. Invest.*, vol. 94, pp. 2036–2044, 1994.

"Role of the Early Response Gene Cyclooxygenase (Cox–2) in Angiogenesis", Chemical Abstracts 125:297565.

Abstract XP002061819 (Doc. Opthalmol., 57/3, pp. 215–262, 1984).

Abstract XP002061818 (Expert Opin. Invest. Drugs, 5/12, pp. 1617–1637, 1996).

Chemical Abstracts 125:297,565, "Role of the Early Response Gene Cyclooxygenase (Cox–2) in Angiogenesis", Feb. 1996.

Huang et al, "Expert Opinion on Investigational Drugs", pp. 243–249, Mar. 1995.

METHOD OF USING CYCLOOXYGENASE-2 INHIBITORS AS ANTI-ANGIOGENIC AGENTS

FIELD OF THE INVENTION

This invention is in the field of the prevention and treatment of angiogenesis. More specifically, this invention relates to the use of cyclooxygenase-2 inhibitors or derivatives thereof in preventing and treating angiogenesis-related disorders.

BACKGROUND OF THE INVENTION

Prostaglandins play a major role in the inflammation process and the inhibition of prostaglandin production, especially production of $PGG_2$, $PGH_2$ and $PGE_2$, has been a common target of anti-inflammatory drug discovery. However, common non-steroidal anti-inflammatory drugs (NSAID's) that are active in reducing the prostaglandin-induced pain and swelling associated with the inflammation process are also active in affecting other prostaglandin-regulated processes not associated with the inflammation process. Thus, use of high doses of most common NSAID's can produce severe side effects, including life threatening ulcers, that limit their therapeutic potential. An alternative to NSAID's is the use of corticosteroids, which also produce severe adverse effects, especially when long term therapy is involved.

NSAIDs have been found to prevent the production of prostaglandins by inhibiting enzymes in the human arachidonic acid/prostaglandin pathway, including the enzyme cyclooxygenase (COX). The recent discovery of an inducible enzyme associated with inflammation (named "cyclooxygenase-2 (COX-2)" or "prostaglandin G/H synthase III") provides a viable target of inhibition which more effectively reduces inflammation and produces fewer and less drastic side effects.

Angiogenesis is the development of new blood vessels into a tissue or organ. Under normal conditions, angiogenesis is observed in wound healing and embryonal development. Uncontrolled angiogenesis is associated with neoplastic disease, tumor metastasis and other angiogenesis-related diseases.

Although originally developed for their anti-inflammatory properties, glucocorticoids are now recognized to have a wide variety of therapeutic uses. For example, many steroids with anti-inflammatory activity inhibit angiogenesis (U.S. Pat. No. 5,646,136).

Compounds which selectively inhibit cyclooxygenase-2 have been described in U.S. Pat. Nos. 5,380,738, 5,344,991, 5,393,790, 5,434,178, 5,474,995, 5,475,018, 5,510,368 and WO documents WO96/06840, WO95/21817, WO96/03388, WO96/03387, WO96/03392, WO96/25405, WO96/24584, WO96/03385, WO96/16934, WO95/15316, WO94/15932, WO94/27980, WO95/00501, WO94/13635, WO94/20480, and WO94/26731.

[Pyrazol-1-yl]benzenesulfonamides have been described as inhibitors of cyclooxygenase-2 and have shown promise in the treatment of inflammation, arthritis, and pain, with minimal side effects in pre-clinical and clinical trials. Their use for preventing colon cancer has been described in U.S. Pat. No. 5,760,068. However, their use for treating or preventing angiogenesis-related diseases has not been previously described.

There have been several publications describing the benefits of inhibiting angiogenesis. WO patent publication No. 96/19469 describes that COX-2 inhibitors would be useful to prevent and/or treat tumor angiogenesis and diabetic retinopathy.

The present invention is directed to the use of inhibitors of cyclooxygenase-2 for the treatment and prevention of tumor growth and metastasis that are dependent on the angiogenic process. In addition, the treatment and prevention of non-neoplastic angiogenesis-related disorders, such as retinopathies, and endometriosis is also included.

DETAILED DESCRIPTION OF THE INVENTION

The present invention provides a method for treating or preventing angiogenesis-related disorders in a subject in need of such treatment or prevention, the method comprises treating the subject with a therapeutically effective amount of a cyclooxygenase-2 inhibitor or derivative or pharmaceutically-acceptable salt thereof.

The method above would be useful for, but not limited to, the treatment of angiogenesis-related disorders in a subject. According to the present invention, the compounds of Formula I are administered to a subject in need of angiogenesis inhibition. The method would be useful for treatment of neoplasia, including metastasis; ophthalmological conditions such as corneal graft rejection, ocular neovascularization, retinal neovascularization including neovascularization following injury or infection, diabetic retinopathy, retrolental fibroplasia and neovascular glaucoma; ulcerative diseases such as gastric ulcer; pathological, but non-malignant, conditions such as hemangiomas, including infantile hemaginomas, angiofibroma of the nasopharynx and avascular necrosis of bone; and disorders of the female reproductive system such as endometriosis.

The term "treatment" includes partial or total inhibition of angiogenesis, including neoplastic growth, spreading or metastasis, as well as partial or total destruction of the neoplastic cells.

The term "prevention" includes either preventing the onset of clinically evident angiogenesis altogether or preventing the onset of a preclinically evident stage of angiogenesis in individuals at risk. Also intended to be encompassed by this definition is the prevention of metastasis of malignant cells or to arrest or reverse the progression of malignant cells. This includes prophylactic treatment of those at risk of developing angiogenesis.

The phrase "therapeutically-effective" is intended to qualify the amount of each agent which will achieve the goal of improvement in disease severity and the frequency of incidence over treatment of each agent by itself, while avoiding adverse side effects typically associated with alternative therapies.

The term "subject" for purposes of treatment includes any human or animal subject who has any one of the known angiogenesis-related disorders. For methods of prevention, the subject is any human or animal subject, and preferably is a human subject who is at risk for obtaining an angiogenesis-related disorder, such as metastasis. The subject may be at risk due to exposure to carcinogenic agents, being genetically predisposed to have the angiogenesis, and the like. Besides being useful for human treatment, these compounds are also useful for veterinary treatment of mammals, including companion animals and farm animals, such as, but not limited to, horses, dogs, cats, cows, sheep and pigs. Preferably, subject means a human.

Inhibitors of the cyclooxygenase pathway in the metabolism of arachidonic acid used in the prevention and treatment of angiogenesis may inhibit enzyme activity through a variety of mechanisms. By the way of example, the inhibitors used in the methods described herein may block the enzyme activity directly by acting as a substrate for the enzyme. The use of cyclooxygenase-2 selective inhibitors is highly advantageous in that it minimize the gastric side effects that can occur with non-selective NSAID's, especially where prolonged prophylactic treatment is expected.

The term "cyclooxygenase-2 inhibitor" denotes a compound able to inhibit cyclooxygenase-2 without significant inhibition of cyclooxygenase-1. Preferably, it includes compounds which have a cyclooxygenase-2 $IC_{50}$ of less than about 0.2 $\mu$M, and also have a selectivity ratio of cyclooxygenase-2 inhibition over cyclooxygenase-1 inhibition of at least 50, and more preferably of at least 100. Even more preferably, the compounds have a cyclooxygenase-1 $IC_{50}$ of greater than about 1 $\mu$M, and more preferably of greater than 10 $\mu$M.

The method provided herein relates to the use of cyclooxygenase-2 inhibitors or derivatives thereof in the prevention and treatment of angiogenesis. In the preferred embodiments, the cyclooxygenase-2 inhibitor is selected from compounds of Formula I

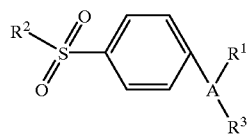

I wherein A is a substituent selected from oxazolyl, isoxazolyl, thienyl, dihydrofuryl, furyl, pyrrolyl, pyrazolyl, thiazolyl, imidazolyl, isothiazolyl, cyclopentenyl, phenyl and pyridyl;

wherein $R^1$ is at least one substituent selected from heterocyclyl, cycloalkyl, cycloalkenyl and aryl, wherein $R^1$ is optionally substituted at a substitutable position with one or more radicals selected from alkyl, haloalkyl, cyano, carboxyl, alkoxycarbonyl, hydroxyl, hydroxyalkyl, haloalkoxy, amino, alkylamino, arylamino, nitro, alkoxyalkyl, alkylsulfinyl, halo, alkoxy and alkylthio;

wherein $R^2$ is methyl or amino; and wherein $R^3$ is a radical selected from hydrido, halo, alkyl, alkenyl, alkynyl, oxo, cyano, carboxyl, cyanoalkyl, heterocyclyloxy, alkyloxy, alkylthio, alkylcarbonyl, cycloalkyl, aryl, haloalkyl, heterocyclyl, cycloalkenyl, aralkyl, heterocyclylalkyl, acyl, alkylthioalkyl, hydroxyalkyl, alkoxycarbonyl, arylcarbonyl, aralkylcarbonyl, aralkenyl, alkoxyalkyl, arylthioalkyl, aryloxyalkyl, aralkylthioalkyl, aralkoxyalkyl, alkoxyaralkoxyalkyl, alkoxycarbonylalkyl, aminocarbonyl, aminocarbonylalkyl, alkylaminocarbonyl, N-arylaminocarbonyl, N-alkyl-N-arylaminocarbonyl, alkylaminocarbonylalkyl, carboxyalkyl, alkylamino, N-arylamino, N-aralkylamino, N-alkyl-N-aralkylamino, N-alkyl-N-arylamino, aminoalkyl, alkylaminoalkyl, N-arylaminoalkyl, N-aralkylaminoalkyl, N-alkyl-N-aralkylaminoalkyl, N-alkyl-N-arylaminoalkyl, aryloxy, aralkoxy, arylthio, aralkylthio, alkylsulfinyl, alkylsulfonyl, aminosulfonyl, alkylaminosulfonyl, N-arylaminosulfonyl, arylsulfonyl, N-alkyl-N-arylaminosulfonyl; or a pharmaceutically-acceptable salt thereof.

A preferred class of compounds which inhibit cyclooxygenase-2 consists of compounds of Formula I wherein A is selected from oxazolyl, isoxazolyl, pyrazolyl, imidazolyl, cyclopentenyl, phenyl, and pyridyl; wherein $R^1$ is selected from 5- and 6-membered heterocyclyl, lower cycloalkyl, lower cycloalkenyl and aryl selected from phenyl, biphenyl and naphthyl, wherein $R^1$ is optionally substituted at a substitutable position with one or more radicals selected from lower alkyl, lower haloalkyl, cyano, carboxyl, lower alkoxycarbonyl, hydroxyl, lower hydroxyalkyl, lower haloalkoxy, amino, lower alkylamino, phenylamino, lower alkoxyalkyl, lower alkylsulfinyl, halo, lower alkoxy and lower alkylthio; wherein $R^2$ is methyl or amino; and wherein $R^3$ is a radical selected from hydrido, oxo, cyano, carboxyl, lower alkoxycarbonyl, lower carboxyalkyl, lower cyanoalkyl, halo, lower alkyl, lower alkyloxy, lower cycloalkyl, phenyl, lower haloalkyl, 5- or 6-membered heterocyclyl, lower hydroxyalkyl, lower aralkyl, acyl, phenylcarbonyl, lower alkoxyalkyl, 5- or 6-membered heteroaryloxy, aminocarbonyl, lower alkylaminocarbonyl, lower alkylamino, lower aminoalkyl, lower alkylaminoalkyl, phenyloxy, and lower aralkoxy; or a pharmaceutically-acceptable salt thereof.

A more preferred class of compounds which inhibit cyclooxygenase-2 consists of compounds of Formula I wherein A is selected from oxazolyl, isoxazolyl, pyrazolyl, imidazolyl and cyclopentenyl; wherein $R^1$ is selected from pyridyl optionally substituted at a substitutable position with one or more methyl radicals, and phenyl optionally substituted at a substitutable position with one or more radicals selected from methyl, ethyl, isopropyl, butyl, tert-butyl, isobutyl, pentyl, hexyl, fluoromethyl, difluoromethyl, trifluoromethyl, cyano, carboxyl, methoxycarbonyl, ethoxycarbonyl, hydroxyl, hydroxymethyl, trifluoromethoxy, amino, N-methylamino, N,N-dimethylamino, N-ethylamino, N,N-dipropylamino, N-butylamino, N-methyl-N-ethylamino, phenylamino, methoxymethyl, methylsulfinyl, fluoro, chloro, bromo, methoxy, ethoxy, propoxy, n-butoxy, pentoxy, and methylthio; wherein $R^2$ is methyl or amino; and wherein $R^3$ is a radical selected from hydrido, oxo, cyano, carboxyl, methoxycarbonyl, ethoxycarbonyl, carboxypropyl, carboxymethyl, carboxyethyl, cyanomethyl, fluoro, chloro, bromo, methyl, ethyl, isopropyl, butyl, tert-butyl, isobutyl, pentyl, hexyl, difluoromethyl, trifluoromethyl, pentafluoroethyl, heptafluoropropyl, difluoroethyl, difluoropropyl, methoxy, ethoxy, propoxy, n-butoxy, pentoxy, cyclohexyl, phenyl, pyridyl, thienyl, thiazolyl, oxazolyl, furyl, pyrazinyl, hydroxylmethyl, hydroxylpropyl, benzyl, formyl, phenylcarbonyl, methoxymethyl, furylmethyloxy, aminocarbonyl, N-methylaminocarbonyl, N,N-dimethylaminocarbonyl, N,N-dimethylamino, N-ethylamino, N,N-dipropylamino, N-butylamino, N-methyl-N-ethylamino, aminomethyl, N,N-dimethylaminomethyl, N-methyl-N-ethylaminomethyl, benzyloxy, and phenyloxy; or a pharmaceutically-acceptable salt thereof.

A family of specific compounds of particular interest within Formula I consists of compounds and pharmaceutically-acceptable salts thereof as follows:

5-(4-fluorophenyl)-1-[4-(methylsulfonyl)phenyl]-3-(trifluoromethyl) pyrazole;

4-(4-fluorophenyl)-5-[4-(methylsulfonyl)phenyl]-1-phenyl-3-(trifluoromethyl) pyrazole;

4-(5-(4-chlorophenyl)-3-(4-methoxyphenyl)-1H-pyrazol-1-yl)benzenesulfonamide 4-(3,5-bis(4-methylphenyl)-1H-pyrazol-1-yl)
benzenesulfonamide;
4-(5-(4-chlorophenyl)-3-phenyl-1H-pyrazol-1-yl)
benzenesulfonamide;
4-(3,5-bis(4-methoxyphenyl)-1H-pyrazol-1-yl)
benzenesulfonamide;
4-(5-(4-chlorophenyl)-3-(4-methylphenyl)-1H-pyrazol-1-yl)benzenesulfonamide;
4-(5-(4-chlorophenyl)-3-(4-nitrophenyl)-1H-pyrazol-1-yl)benzenesulfonamide;
4-(5-(4-chlorophenyl)-3-(5-chloro-2-thienyl)-1H-pyrazol-1-yl)benzenesulfonamide;
4-(4-chloro-3,5-diphenyl-1H-pyrazol-1-yl)
benzenesulfonamide
4-[5-(4-chlorophenyl)-3-(trifluoromethyl)-1H-pyrazol-1-yl]
benzenesulfonamide;
4-[5-phenyl-3-(trifluoromethyl)-1H-pyrazol-1-yl]
benzenesulfonamide;
4-[5-(4-fluorophenyl)-3-(trifluoromethyl)-1H-pyrazol-1-yl]
benzenesulfonamide;
4-[5-(4-methoxyphenyl)-3-(trifluoromethyl)-1H-pyrazol-1-yl]benzenesulfonamide;
4-[5-(4-chlorophenyl)-3-(difluoromethyl)-1H-pyrazol-1-yl]
benzenesulfonamide;
4-[5-(4-methylphenyl)-3-(trifluoromethyl)-1H-pyrazol-1-yl]benzenesulfonamide;
4-[4-chloro-5-(4-chlorophenyl)-3-(trifluoromethyl)-1H-pyrazol-1-yl]benzenesulfonamide;
4-[3-(difluoromethyl)-5-(4-methylphenyl)-1H-pyrazol-1-yl]
benzenesulfonamide;
4-[3-(difluoromethyl)-5-phenyl-1H-pyrazol-1-yl]
benzenesulfonamide;
4-[3-(difluoromethyl)-5-(4-methoxyphenyl)-1H-pyrazol-1-yl]benzenesulfonamide;
4-[3-cyano-5-(4-fluorophenyl)-1H-pyrazol-1-yl]
benzenesulfonamide;
4-[3-(difluoromethyl)-5-(3-fluoro-4-methoxyphenyl)-1H-pyrazol-1-yl]benzenesulfonamide;
4-[5-(3-fluoro-4-methoxyphenyl)-3-(trifluoromethyl)-1H-pyrazol-1-yl]benzenesulfonamide;
4-[4-chloro-5-phenyl-1H-pyrazol-1-yl]
benzenesulfonamide;
4-[5-(4-chlorophenyl)-3-(hydroxymethyl)-1H-pyrazol-1-yl]
benzenesulfonamide;
4-[5-(4-(N,N-dimethylamino)phenyl)-3-(trifluoromethyl)-1H-pyrazol-1-yl]benzenesulfonamide;
2-methyl-4-[1-[4-(methylsulfonyl)phenyl-4-(trifluoromethyl)-1H-imidazol-2-yl]pyridine;
2-methyl-6-[1-[4-(methylsulfonyl)phenyl-4-(trifluoromethyl)-1H-imidazol-2-yl]pyridine;
4-[2-(6-methylpyridin-3-yl)-4-(trifluoromethyl)-1H-imidazol-1-yl]benzenesulfonamide;
4-[2-(6-methylpyridin-3-yl)-4-(trifluoromethyl)-1H-imidazol-1-yl]benzenesulfonamide;
2-(3,4-difluorophenyl)-1-[4-(methylsulfonyl)phenyl]-4-(trifluoromethyl)-1H-imidazole;
4-[2-(4-methylphenyl)-4-(trifluoromethyl)-1H-imidazol-1-yl]benzenesulfonamide;
2-(4-chlorophenyl)-1-[4-(methylsulfonyl)phenyl]-4-methyl-1H-imidazole;
2-(4-chlorophenyl)-1-[4-(methylsulfonyl)phenyl]-4-phenyl-1H-imidazole;
2-(4-chlorophenyl)-4-(4-fluorophenyl)-1-[4-(methylsulfonyl)phenyl]-1H-imidazole;
2-(3-fluoro-4-methoxyphenyl)-1-[4-(methylsulfonyl)phenyl-4-(trifluoromethyl)-1H-imidazole;
1-[4-(methylsulfonyl)phenyl]-2-phenyl-4-trifluoromethyl-1H-imidazole;
2-(4-methylphenyl)-1-[4-(methylsulfonyl)phenyl]-4-trifluoromethyl-1H-imidazole;
4-[2-(3-chloro-4-methylphenyl)-4-(trifluoromethyl)-1H-imidazol-1-yl]benzenesulfonamide;
2-(3-fluoro-5-methylphenyl)-1-[4-(methylsulfonyl)phenyl]-4-(trifluoromethyl)-1H-imidazole;
4-[2-(3-fluoro-5-methylphenyl)-4-(trifluoromethyl)-1H-imidazol-1-yl]benzenesulfonamide;
2-(3-methylphenyl)-1-[4-(methylsulfonyl)phenyl]-4-trifluoromethyl-1H-imidazole;
4-[2-(3-methylphenyl)-4-trifluoromethyl-1H-imidazol-1-yl]
benzenesulfonamide;
1-[4-(methylsulfonyl)phenyl]-2-(3-chlorophenyl)-4-trifluoromethyl-1H-imidazole;
4-[2-(3-chlorophenyl)-4-trifluoromethyl-1H-imidazol-1-yl]
benzenesulfonamide;
4-[2-phenyl-4-trifluoromethyl-1H-imidazol-1-yl]
benzenesulfonamide;
4-[2-(4-methoxy-3-chlorophenyl)-4-trifluoromethyl-1H-imidazol-1-yl]benzenesulfonamide;
1-allyl-4-(4-fluorophenyl)-3-[4-(methylsulfonyl)phenyl]-5-(trifluoromethyl)-1H-pyrazole;
4-[1-ethyl-4-(4-fluorophenyl)-5-(trifluoromethyl)-1H-pyrazol-3-yl]benzenesulfonamide;
N-phenyl-[4-(4-luorophenyl)-3-[4-(methylsulfonyl)
phenyl]-5-(trifluoromethyl)-1H-pyrazol-1-yl]acetamide;
ethyl [4-(4-fluorophenyl)-3-[4-(methylsulfonyl)phenyl]-5-(trifluoromethyl)-1H-pyrazol-1-yl]acetate;
4-(4-fluorophenyl)-3-[4-(methylsulfonyl)phenyl]-1-(2-phenylethyl)-1H-pyrazole;
4-(4-fluorophenyl)-3-[4-(methylsulfonyl)phenyl]-1-(2-phenylethyl)-5-(trifluoromethyl)pyrazole;
1-ethyl-4-(4-fluorophenyl)-3-[4-(methylsulfonyl)phenyl]-5-(trifluoromethyl)-1H-pyrazole;
5-(4-fluorophenyl)-4-(4-methylsulfonylphenyl)-2-trifluoromethyl-1H-imidazole;
4-[4-(methylsulfonyl)phenyl]-5-(2-thiophenyl)-2-(trifluoromethyl)-1H-imidazole;
5-difluoromethyl-4-(4-methylsulfonylphenyl)-3-phenylisoxazole;
4-[3-ethyl-5-phenylisoxazol-4-yl]benzenesulfonamide;
4-[5-difluoromethyl-3-phenylisoxazol-4-yl]
benzenesulfonamide;
4-[5-hydroxymethyl-3-phenylisoxazol-4-yl]
benzenesulfonamide;
4-[5-methyl-3-phenyl-isoxazol-4-yl]benzenesulfonamide;
1-[2-(4-fluorophenyl)cyclopenten-1-yl]-4-(methylsulfonyl)
benzene;
1-[2-(4-fluoro-2-methylphenyl)cyclopenten-1-yl]-4-(methylsulfonyl)benzene;
1-[2-(4-chlorophenyl)cyclopenten-1-yl]-4-(methylsulfonyl)
benzene;
1-[2-(2,4-dichlorophenyl)cyclopenten-1-yl]-4-(methylsulfonyl)benzene;
1-[2-(4-trifluoromethylphenyl)cyclopenten-1-yl]-4-(methylsulfonyl)benzene;
1-[2-(4-methylthiophenyl)cyclopenten-1-yl]-4-(methylsulfonyl)benzene;
1-[2-(4-fluorophenyl)-4,4-dimethylcyclopenten-1-yl]-4-(methylsulfonyl)benzene;
4-[2-(4-fluorophenyl)-4,4-dimethylcyclopenten-1-yl]
benzenesulfonamide;
1-[2-(4-chlorophenyl)-4,4-dimethylcyclopenten-1-yl]-4-(methylsulfonyl)benzene;
4-[2-(4-chlorophenyl)-4,4-dimethylcyclopenten-1-yl]
benzenesulfonamide;
4-[2-(4-fluorophenyl)cyclopenten-1-yl]
benzenesulfonamide;

4-[2-(4-chlorophenyl)cyclopenten-1-yl]
benzenesulfonamide;
1-[2-(4-methoxyphenyl)cyclopenten-1-yl]-4-
(methylsulfonyl)benzene;
1-[2-(2,3-difluorophenyl)cyclopenten-1-yl]-4-
(methylsulfonyl)benzene;
4-[2-(3-fluoro-4-methoxyphenyl)cyclopenten-1-yl]
benzenesulfonamide;
1-[2-(3-chloro-4-methoxyphenyl)cyclopenten-1-yl]-4-
(methylsulfonyl)benzene;
4-[2-(3-chloro-4-fluorophenyl)cyclopenten-1-yl]
benzenesulfonamide;
4-[2-(2-methylpyridin-5-yl)cyclopenten-1-yl]
benzenesulfonamide;
ethyl 2-[4-(4-fluorophenyl)-5-[4-(methylsulfonyl)phenyl]
oxazol-2-yl]-2-benzyl-acetate;
2-[4-(4-fluorophenyl)-5-[4-(methylsulfonyl)phenyl]oxazol-
2-yl]acetic acid;
2-(tert-butyl)-4-(4-fluorophenyl)-5-[4-(methylsulfonyl)
phenyl]oxazole;
4-(4-fluorophenyl)-5-[4-(methylsulfonyl)phenyl]-2-
phenyloxazole;
4-(4-fluorophenyl)-2-methyl-5-[4-(methylsulfonyl)phenyl]
oxazole; and
4-[5-(3-fluoro-4-methoxyphenyl)-2-trifluoromethyl-4-
oxazolyl]benzenesulfonamide.

A family of specific compounds of more particular interest within Formula I consists of compounds and pharmaceutically-acceptable salts thereof as follows:

4-[5-(4-chlorophenyl)-3-(trifluoromethyl)-1H-pyrazol-1-yl]
benzenesulfonamide;
4-[5-(4-methylphenyl)-3-(trifluoromethyl)-1H-pyrazol-1-
yl]benzenesulfonamide;
4-[5-(3-fluoro-4-methoxyphenyl)-3-(difluoromethyl)-1H-
pyrazol-1-yl]benzenesulfonamide;
3-[1-[4-(methylsulfonyl)phenyl]-4-trifluoromethyl-1H-
imidazol-2-yl]pyridine;
2-methyl-5-[1-[4-(methylsulfonyl)phenyl]-4-
trifluoromethyl-1H-imidazol-2-yl]pyridine;
4-[2-(5-methylpyridin-3-yl)-4-(trifluoromethyl)-1H-
imidazol-1-yl]benzenesulfonamide;
4-[5-methyl-3-phenylisoxazol-4-yl]benzenesulfonamide;
4-[5-hydroxymethyl-3-phenylisoxazol-4-yl]
benzenesulfonamide;
[2-trifluoromethyl-5-(3,4-difluorophenyl)-4-oxazolyl]
benzenesulfonamide;
4-[2-methyl-4-phenyl-5-oxazolyl]benzenesulfonamide; and
4-[5-(3-fluoro-4-methoxyphenyl-2-trifluoromethyl)-4-
oxazolyl]benzenesulfonamide.

A subclass of cyclooxygenase-2 inhibitors is selected from compounds of Formula II

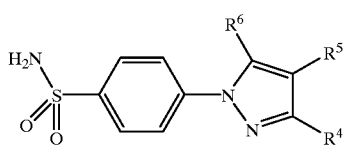

II wherein $R^4$ is selected from hydrido, alkyl, haloalkyl, alkoxycarbonyl, cyano, cyanoalkyl, carboxyl, aminocarbonyl, alkylaminocarbonyl, cycloalkylaminocarbonyl, arylaminocarbonyl, carboxyalkylaminocarbonyl, carboxyalkyl, aralkoxycarbonylalkylaminocarbonyl, aminocarbonylalkyl, alkoxycarbonylcyanoalkenyl and hydroxyalkyl;

wherein $R^5$ is selected from hydrido, alkyl, cyano, hydroxyalkyl, cycloalkyl, alkylsulfonyl and halo; and wherein $R^6$ is selected from aralkenyl, aryl, cycloalkyl, cycloalkenyl and heterocyclic; wherein $R^6$ is optionally substituted at a substitutable position with one or more radicals selected from halo, alkylthio, alkylsulfonyl, cyano, nitro, haloalkyl, alkyl, hydroxyl, alkenyl, hydroxyalkyl, carboxyl, cycloalkyl, alkylamino, dialkylamino, alkoxycarbonyl, aminocarbonyl, alkoxy, haloalkoxy, sulfamyl, heterocyclic and amino;

or a pharmaceutically-acceptable salt or derivative thereof.

A class of compounds of particular interest consists of those compounds of Formula II wherein $R^4$ is selected from lower haloalkyl; wherein $R^5$ is hydrido; and wherein $R^6$ is selected from phenyl optionally substituted at a substitutable position with one or more radicals selected from halo, lower alkyl and lower alkoxy; or a pharmaceutically-acceptable salt or derivative thereof.

A family of specific compounds of particular interest within Formula I consists of compounds, derivatives and pharmaceutically-acceptable salts thereof as follows:

4-[5-(4-chlorophenyl)-3-(trifluoromethyl)-1H-pyrazol-1-yl]
benzenesulfonamide;
4-[5-phenyl-3-(trifluoromethyl)-1H-pyrazol-1-yl]
benzenesulfonamide;
4-[5-(4-fluorophenyl)-3-(trifluoromethyl)-1H-pyrazol-1-yl]
benzenesulfonamide;
4-[5-(4-methoxyphenyl)-3-(trifluoromethyl)-1H-pyrazol-1-
yl]benzenesulfonamide;
4-[5-(4-chlorophenyl)-3-(difluoromethyl)-1H-pyrazol-1-yl]
benzenesulfonamide;
4-[5-(4-methylphenyl)-3-(trifluoromethyl)-1H-pyrazol-1-
yl]benzenesulfonamide;
4-[3-(difluoromethyl)-5-(4-methylphenyl)-1H-pyrazol-1-yl]
benzenesulfonamide;
4-[3-(difluoromethyl)-5-phenyl-1H-pyrazol-1-yl]
benzenesulfonamide;
4-[3-(difluoromethyl)-5-(4-methoxyphenyl)-1H-pyrazol-1-
yl]benzenesulfonamide;
4-[3-(difluoromethyl)-5-(3-fluoro-4-methoxyphenyl)-1H-
pyrazol-1-yl]benzenesulfonamide; and
4-[5-(3-fluoro-4-methoxyphenyl)-3-(trifluoromethyl)-1H-
pyrazol-1-yl]benzenesulfonamide.

A family of specific compounds of more particular interest within Formula I consists of compounds and pharmaceutically-acceptable salts or derivatives thereof as follows:

4-[5-(4-methylphenyl)-3-(trifluoromethyl)-1H-pyrazol-1-
yl]benzenesulfonamide;
4-[5-(4-chlorophenyl)-3-(difluoromethyl)-1H-pyrazol-1-yl]
benzenesulfonamide; and
4-[5-(3-fluoro-4-methoxyphenyl)-3-(difluoromethyl)-1H-
pyrazol-1-yl]benzenesulfonamide.

Derivatives are intended to encompass any compounds which are structurally related to the cyclooxygenase-2 inhibitors or which possess the substantially equivalent biologic activity. By way of example, such inhibitors may include, but are not limited to, prodrugs thereof. Such compounds can be formed in vivo, such as by metabolic mechanisms.

The term "hydrido" denotes a single hydrogen atom (H). This hydrido radical may be attached, for example, to an oxygen atom to form a hydroxyl radical or two hydrido radicals may be attached to a carbon atom to form a methylene (—CH$_2$—) radical. Where used, either alone or within other terms such as "haloalkyl", "alkylsulfonyl", "alkoxyalkyl" and "hydroxyalkyl", the term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about six carbon atoms. Examples of such radicals include methyl, ethyl, n-propyl, isopropyl, n-butyl, isobutyl, sec-butyl, tert-butyl, pentyl, iso-amyl, hexyl and the like. The term "alkenyl" embraces linear or branched radicals having at least one carbon-carbon double bond of two to about twenty carbon atoms or, preferably, two to about twelve carbon atoms. More preferred alkenyl radicals are "lower alkenyl" radicals having two to about six carbon atoms. Examples of alkenyl radicals include ethenyl, propenyl, allyl, propenyl, butenyl and 4-methylbutenyl. The term "alkynyl" denotes linear or branched radicals having two to about twenty carbon atoms or, preferably, two to about twelve carbon atoms. More preferred alkynyl radicals are "lower alkynyl" radicals having two to about ten carbon atoms. Most preferred are lower alkynyl radicals having two to about six carbon atoms. Examples of such radicals include propargyl, butynyl, and the like. The terms "alkenyl", "lower alkenyl", embrace radicals having "cis" and "trans" orientations, or alternatively, "E" and "Z" orientations. The term "cycloalkyl" embraces saturated carbocyclic radicals having three to twelve carbon atoms. More preferred cycloalkyl radicals are "lower cycloalkyl" radicals having three to about eight carbon atoms. Examples of such radicals include cyclopropyl, cyclobutyl, cyclopentyl and cyclohexyl. The term "cycloalkenyl" embraces partially unsaturated carbocyclic radicals having three to twelve carbon atoms. More preferred cycloalkenyl radicals are "lower cycloalkenyl" radicals having four to about eight carbon atoms. Examples of such radicals include cyclobutenyl, cyclopentenyl, cyclopentadienyl, and cyclohexenyl. The term "halo" means halogens such as fluorine, chlorine, bromine or iodine. The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl", embraces radicals having 1–6 carbon atoms. Examples of haloalkyl radicals include fluoromethyl, difluoromethyl, trifluoromethyl, chloromethyl, dichloromethyl, trichloromethyl, trichloromethyl, pentafluoroethyl, heptafluoropropyl, difluorochloromethyl, dichlorofluoromethyl, difluoroethyl, difluoropropyl, dichloroethyl and dichloropropyl. The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. The terms "alkoxy" and "alkyloxy" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. The term "alkoxyalkyl" embraces alkyl radicals having one or more alkoxy radicals attached to the alkyl radical, that is, to form monoalkoxy-alkyl and dialkoxyalkyl radicals. The "alkoxy" radicals may be further substituted with one or more halo atoms, such as fluoro, chloro or bromo, to provide haloalkoxy radicals. More preferred haloalkoxy radicals are "lower haloalkoxy" radicals having one to six carbon atoms and one or more halo radicals. Examples of such radicals include fluoromethoxy, chloromethoxy, trifluoromethoxy, trifluoroethoxy, fluoroethoxy and fluoropropoxy. The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl. Aryl moieties may also be substituted at a substitutable position with one or more substituents selected independently from alkyl, alkoxyalkyl, alkylaminoalkyl, carboxyalkyl, alkoxycarbonylalkyl, aminocarbonylalkyl, alkoxy, aralkoxy, hydroxyl, amino, halo, nitro, alkylamino, acyl, cyano, carboxy, aminocarbonyl, alkoxycarbonyl and aralkoxycarbonyl. The term "heterocyclyl" embraces saturated, partially unsaturated and unsaturated heteroatom-containing ring-shaped radicals, where the heteroatoms may be selected from nitrogen, sulfur and oxygen. Examples of saturated heterocyclyl radicals include saturated 3 to 6-membered heteromonocylic group containing 1 to 4 nitrogen atoms (e.g. pyrrolidinyl, imidazolidinyl, piperidino, piperazinyl, etc.); saturated 3 to 6-membered heteromonocyclic group containing 1 to 2 oxygen atoms and 1 to 3 nitrogen atoms (e.g. morpholinyl, etc.); saturated 3 to 6-membered heteromonocyclic group containing 1 to 2 sulfur atoms and 1 to 3 nitrogen atoms (e.g., thiazolidinyl, etc.). Examples of partially unsaturated heterocyclyl radicals include dihydrothiophene, dihydropyran, dihydrofuran and dihydrothiazole. The term "heteroaryl" embraces unsaturated heterocyclyl radicals. Examples of unsaturated heterocyclyl radicals, also termed "heteroaryl" radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.) tetrazolyl (e.g. 1H-tetrazolyl, 2H-tetrazolyl, etc.), etc.; unsaturated condensed heterocyclyl group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b] pyridazinyl, etc.), etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclyl group containing 1 to 2 oxygen atoms and 1 to 3 nitrogen atoms (e.g. benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1,2,4- thiadiazolyl, 1,3,4-thiadiazolyl, 1,2,5-thiadiazolyl, etc.) etc.; unsaturated condensed heterocyclyl group containing 1 to 2 sulfur atoms and 1 to 3 nitrogen atoms (e.g., benzothiazolyl, benzothiadiazolyl, etc.) and the like. The term also embraces radicals where heterocyclyl radicals are fused with aryl radicals.

Examples of such fused bicyclic radicals include benzofuran, benzothiophene, and the like. Said "heterocyclyl group" may have 1 to 3 substituents such as alkyl, hydroxyl, halo, alkoxy, oxo, amino and alkylamino. The term "alkylthio" embraces radicals containing a linear or branched alkyl radical, of one to about ten carbon atoms attached to a divalent sulfur atom. More preferred alkylthio radicals are "lower alkylthio" radicals having alkyl radicals of one to six carbon atoms. Examples of such lower alkylthio radicals are methylthio, ethylthio, propylthio, butylthio and hexylthio. The term "alkylthioalkyl" embraces radicals containing an alkylthio radical attached through the divalent sulfur atom to an alkyl radical of one to about ten carbon atoms. More preferred alkylthioalkyl radicals are "lower alkylthioalkyl" radicals having alkyl radicals of one to six carbon atoms. Examples of such lower alkylthioalkyl radicals include methylthiomethyl. The term "alkylsulfinyl" embraces mradicals containing a linear or branched alkyl radical, of one to ten carbon atoms, attached to a divalent —S(=O)— radical. More preferred alkylsulfinyl radicals are "lower alkylsulfinyl" radicals having alkyl radicals of one to six carbon atoms. Examples of such lower alkylsulfinyl radicals include methylsulfinyl, ethylsulfinyl, butylsulfinyl and hexylsulfinyl. The term "sulfonyl", whether used alone or linked to other terms such as alkylsulfonyl, denotes respectively divalent radicals —SO$_2$—. "Alkylsulfonyl" embraces alkyl radicals attached to a sulfonyl radical, where alkyl is defined as above. More preferred alkylsulfonyl radicals are "lower alkylsulfonyl" radicals having one to six carbon atoms. Examples of such lower alkylsulfonyl radicals include methylsulfonyl, ethylsulfonyl and propylsulfonyl.

The "alkylsulfonyl" radicals may be further substituted with one or more halo atoms, such as fluoro, chloro or bromo, to provide haloalkylsulfonyl radicals. The terms "sulfamyl", "aminosulfonyl" and "sulfonamidyl" denote NH$_2$O$_2$S—. The term "acyl" denotes a radical provided by the residue after removal of hydroxyl from an organic acid. Examples of such acyl radicals include alkanoyl and aroyl radicals. Examples of such lower alkanoyl radicals include formyl, acetyl, propionyl, butyryl, isobutyryl, valeryl, isovaleryl, pivaloyl, hexanoyl, trifluoroacetyl. The term "carbonyl", whether used alone or with other terms, such as "alkoxycarbonyl", denotes —(C=O)—. The term "aroyl" embraces aryl radicals with a carbonyl radical as defined above. Examples of aroyl include benzoyl, naphthoyl, and the like and the aryl in said aroyl may be additionally substituted. The terms "carboxy" or "carboxyl", whether used alone or with other terms, such as "carboxyalkyl", denotes —CO$_2$H.

The term "carboxyalkyl" embraces alkyl radicals substituted with a carboxy radical. More preferred are "lower carboxyalkyl" which embrace lower alkyl radicals as defined above, and may be additionally substituted on the alkyl radical with halo. Examples of such lower carboxyalkyl radicals include carboxymethyl, carboxyethyl and carboxypropyl. The term "alkoxycarbonyl" means a radical containing an alkoxy radical, as defined above, attached via an oxygen atom to a carbonyl radical. More preferred are "lower alkoxycarbonyl" radicals with alkyl porions having 1 to 6 carbons. Examples of such lower alkoxycarbonyl (ester) radicals include substituted or unsubstituted methoxycarbonyl, ethoxycarbonyl, propoxycarbonyl, butoxycarbonyl and hexyloxycarbonyl. The terms "alkylcarbonyl", "arylcarbonyl" and "aralkylcarbonyl" include radicals having alkyl, aryl and aralkyl radicals, as defined above, attached to a carbonyl radical. Examples of such radicals include substituted or unsubstituted methylcarbonyl, ethylcarbonyl, phenylcarbonyl and benzylcarbonyl. The term "aralkyl" embraces aryl-substituted alkyl radicals such as benzyl, diphenylmethyl, triphenylmethyl, phenylethyl, and diphenylethyl. The aryl in said aralkyl may be additionally substituted with halo, alkyl, alkoxy, halkoalkyl and haloalkoxy. The terms benzyl and phenylmethyl are interchangeable. The term "heterocyclylalkyl" embraces saturated and partially unsaturated heterocyclyl-substituted alkyl radicals, such as pyrrolidinylmethyl, and heteroaryl-substituted alkyl radicals, such as pyridylmethyl, quinolylmethyl, thienylmethyl, furylethyl, and quinolylethyl. The heteroaryl in said heteroaralkyl may be additionally substituted with halo, alkyl, alkoxy, halkoalkyl and haloalkoxy.

The term "aralkoxy" embraces aralkyl radicals attached through an oxygen atom to other radicals.

The term "aralkoxyalkyl" embraces aralkoxy radicals attached through an oxygen atom to an alkyl radical.

The term "aralkylthio" embraces aralkyl radicals attached to a sulfur atom. The term "aralkylthioalkyl" embraces aralkylthio radicals attached through a sulfur atom to an alkyl radical.

The term "aminoalkyl", embraces alkyl radicals substituted with one or more amino radicals. More preferred are "lower aminoalkyl", radicals. Examples of such radicals include aminomethyl, aminoethyl, and the like. The term "alkylamino" denotes amino groups which have been substituted with one or two alkyl radicals. Preferred are "lower N-alkylamino" radicals having alkyl portions having 1 to 6 carbon atoms. Suitable lower alkylamino may be mono or dialkylamino such as N-methylamino, N-ethylamino, N,N-dimethylamino, N,N-diethylamino or the like. The term "arylamino" denotes amino groups which have been substituted with one or two aryl radicals, such as N-phenylamino. The "arylamino" radicals may be further substituted on the aryl ring portion of the radical. The term "aralkylamino" embraces aralkyl radicals attached through an amino nitrogen atom to other radicals. The terms "N-arylaminoalkyl" and "N-aryl-N-alkyl-aminoalkyl" denote amino groups which have been substituted with one aryl radical or one aryl and one alkyl radical, respectively, and having the amino group attached to an alkyl radical.

Examples of such radicals include N-phenylaminomethyl and N-phenyl-N-methylaminomethyl.

The term "aminocarbonyl" denotes an amide group of the formula —C(=O)NH$_2$. The term "alkylaminocarbonyl" denotes an aminocarbonyl group which has been substituted with one or two alkyl radicals on the amino nitrogen atom. Preferred are "N-alkylaminocarbonyl" "N,N-dialkylaminocarbonyl" radicals. More preferred are "lower N-alkylaminocarbonyl" "lower N,N-dialkylaminocarbonyl" radicals with lower alkyl portions as defined above.

The term "alkylaminoalkyl" embraces radicals having one or more alkyl radicals attached to an aminoalkyl radical. The term "aryloxyalkyl" embraces radicals having an aryl radical attached to an alkyl radical through a divalent oxygen atom. The term "arylthioalkyl" embraces radicals having an aryl radical attached to an alkyl radical through a divalent sulfur atom.

The compounds utilized in the methods of the present invention may be present in the form of free bases or pharmaceutically acceptable acid addition salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, β-hydroxybutyric, salicylic, galactaric and galacturonic acid. Suitable pharmaceutically-acceptable base addition salts of compounds of Formula I include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

GENERAL SYNTHETIC PROCEDURES

The cyclooxygenase-2 inhibitor compounds of the invention can be synthesized according to the following procedures of Schemes I–X, wherein the $R^1$–$R^3$ substituents are as defined for Formula I, above, except where further noted.

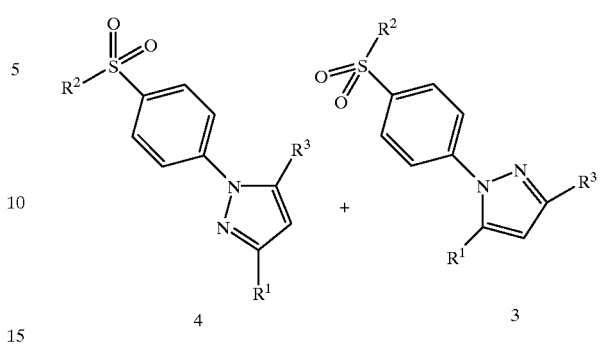

Synthetic Scheme I shows the preparation of cyclooxygenase-2 inhibitor compounds, as described in U.S. Pat. No. 5,521,207 and WQ95/15316, which are incorporated by reference, embraced by Formula I. In step 1, ketone 1 is treated with a base, preferably NaOMe or NaH, and an ester, or ester equivalent, to form the intermediate diketone 2 (in the enol form) which is used without further purification. In step 2, diketone 2 in an anhydrous protic solvent, such as absolute ethanol or acetic acid, is treated with the hydrochloride salt or the free base of a substituted hydrazine at reflux to afford a mixture of pyrazoles 3 and 4. Recrystallization or chromatography affords 3 usually as a solid. Similar pyrazoles can be prepared by methods described in U.S. Pat. Nos. 4,146,721, 5,051,518, 5,134,142 and 4,914,121 which also are incorporated by reference.

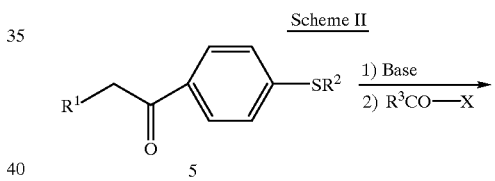

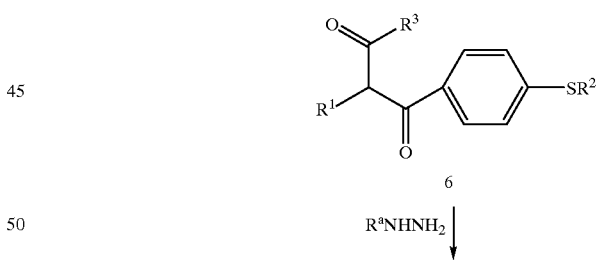

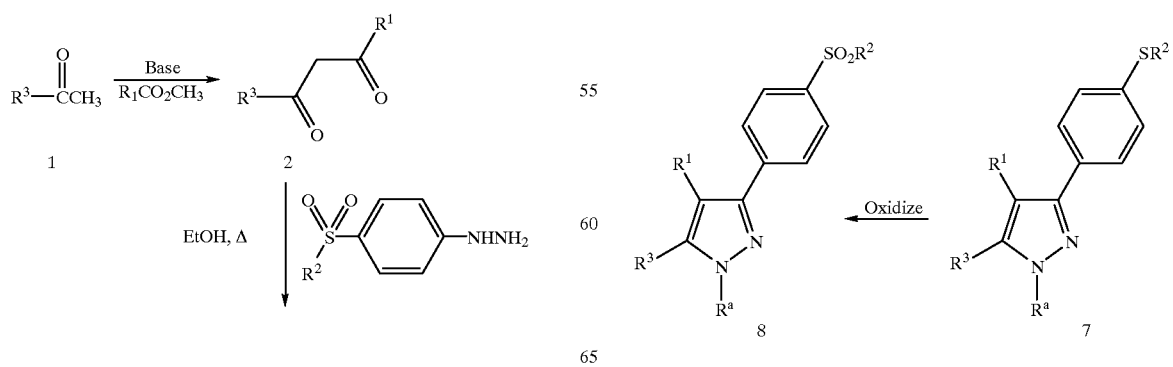

Scheme II shows the four step procedure for forming cyclooxygenase-2 inhibitor pyrazoles 8 as described in U.S. Pat. No. 5,486,534 (where $R^a$ is hydrido or alkyl) from ketones 5. In step 1, ketone 5 is reacted with a base, such as lithium bis(trimethylsilyl)amide or lithium diisopropylamide (LDA) to form the anion. In step 2, the anion is reacted with an acetylating reagent to provide diketone 6. In step 3, the reaction of diketone 6 with hydrazine or a substituted hydrazine, gives pyrazole 7. In step 4, the pyrazole 7 is oxidized with an oxidizing reagent, such as Oxone® (potassium peroxymonosulfate), 3-chloroperbenzoic acid (MCPBA) or hydrogen peroxide, to give a mixture of the desired 3-(alkylsulfonyl)phenyl-pyrazole 8 and the 5-(alkylsulfonyl)phenyl-pyrazole isomer. The desired pyrazole 8, usually a white or pale yellow solid, is obtained in pure form either by chromatography or recrystallization.

Alternatively, diketone 6 can be formed from ketone 5 by treatment with a base, such as sodium hydride, in a solvent, such as dimethylformamide, and further reacting with a nitrile to form an aminoketone. Treatment of the aminoketone with acid forms the diketone 6. Similar pyrazoles can be prepared by methods described in U.S. Pat. No. 3,984,431 which is incorporated by reference.

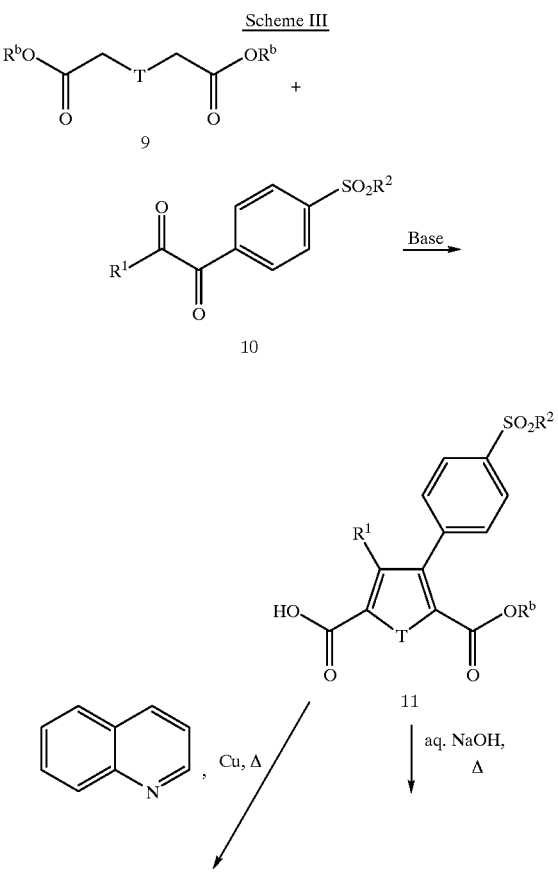

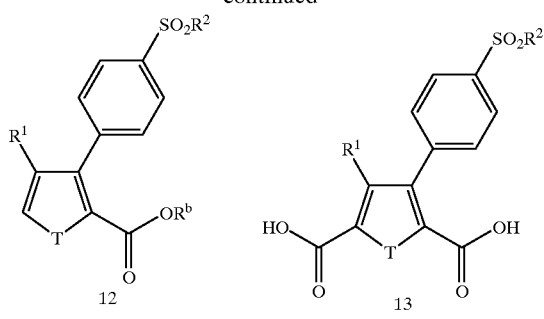

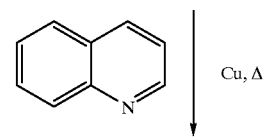

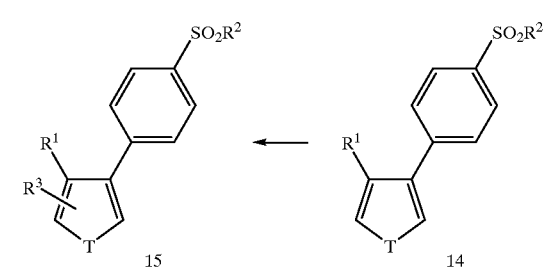

Cyclooxygenase-2 inhibitor diaryl/heteroaryl thiophenes (where T is S, and $R^b$ is alkyl) can be prepared by the methods described in U.S. Pat. Nos. 4,427,693, 4,302,461, 4,381,311, 4,590,205, and 4,820,827, and PCT documents WO 95/00501 and WO94/15932, which are incorporated by reference.

Similar pyrroles (where T is N), furanones and furans (where T is O) can be prepared by methods described in PCT documents WO 95/00501 and WO94/15932, and in EP799,823.

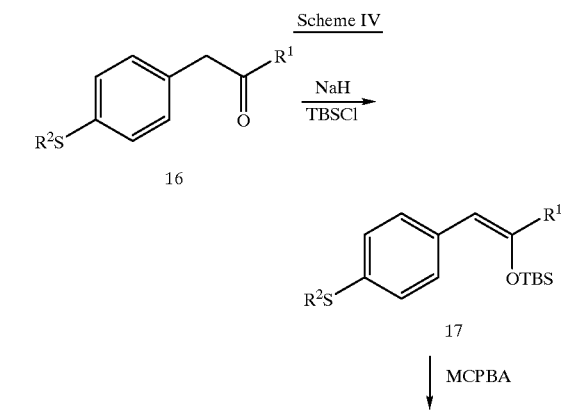

17
-continued

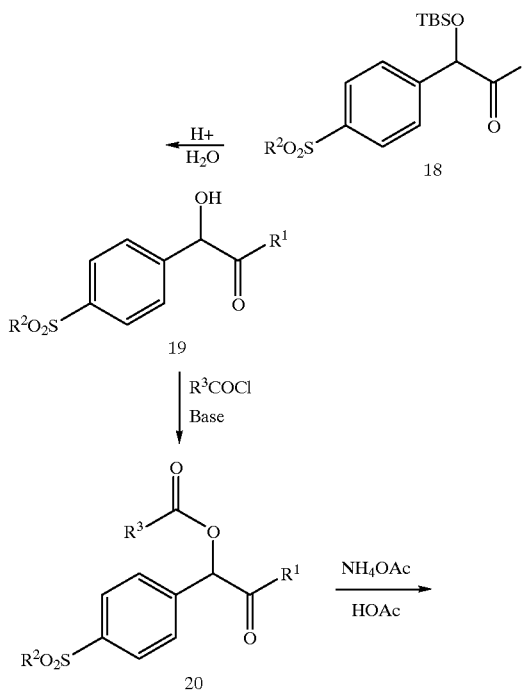

Cyclooxygenase-2 inhibitor diaryl/heteroaryl oxazoles can be prepared by the methods described in U.S. Pat. Nos. 3,743,656, 3,644,499 and 3,647,858, and PCT documents WO 95/00501 and WO94/27980, which are incorporated by reference. Equivalent oxazole compounds can be prepared via WO96/19463 and WO96/19462.

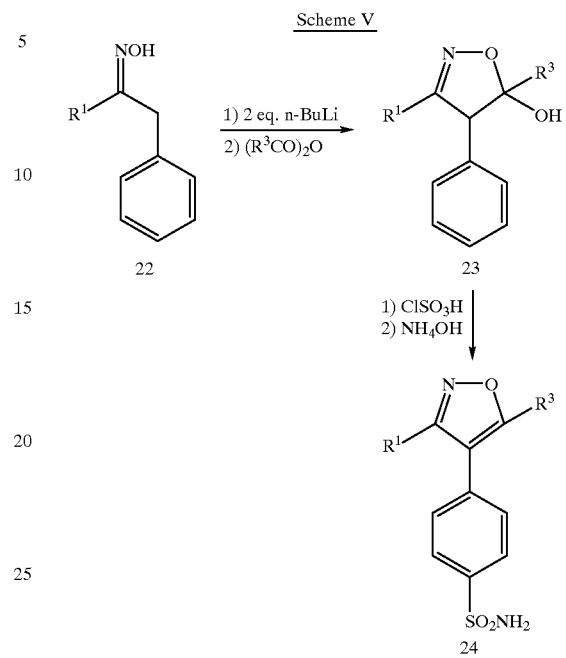

Cyclooxygenase-2 inhibitor diaryl/heteroaryl isoxazoles can be prepared by the methods described in U.S. Pat. No. 5,633,272, PCT documents W)92/05162, and WO92/19604, and European Publication EP 26928 which are incorporated by reference. Sulfonamides 24 can be formed from the hydrated isoxazole 23 in a two step procedure. First, hydrated isoxazole 23 is treated at about 0° C. with two or three equivalents of chlorosulfonic acid to form the corresponding sulfonyl chloride. In step two, the sulfonyl chloride thus formed is treated with concentrated ammonia to provide the sulfonamide derivative 24.

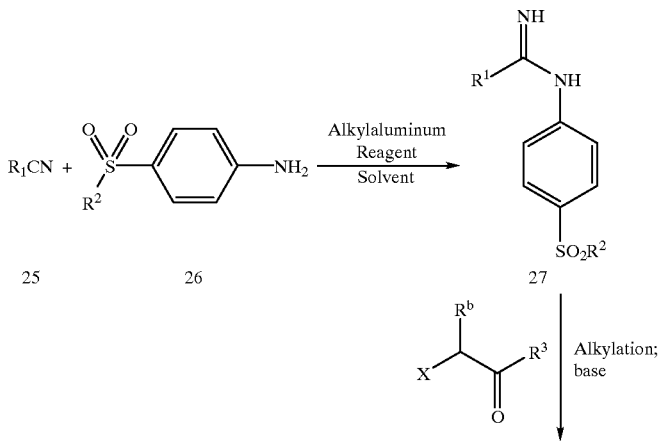

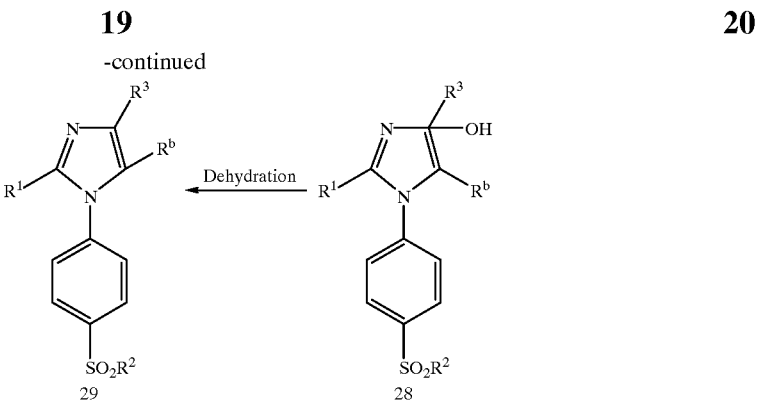

Scheme VI shows the three step preparation of the cyclooxygenase-2 inhibitor imidazoles 29 of the present invention. In step 1, the reaction of substituted nitriles ($R^1CN$) 25 with primary phenylamines 26 in the presence of alkylaluminum reagents such as trimethylaluminum, triethylaluminum, dimethylaluminum chloride, diethylaluminum chloride in the presence of inert solvents such as toluene, benzene, and xylene, gives amidines 27. In step 2, the reaction of amidine 27 with 2-haloketones (where X is Br or Cl) in the presence of bases, such as sodium bicarbonate, potassium carbonate, sodium carbonate, potassium bicarbonate or hindered tertiary amines such as N,N'-diisopropylethylamine, gives the 4,5-dihydroimidazoles 28 (where $R^b$ is alkyl). Some of the suitable solvents for this reaction are isopropanol, acetone and dimethylformamide. The reaction may be carried out at temperatures of about 20° C. to about 90° C. In step 3, the 4,5-dihydroimidazoles 28 may be dehydrated in the presence of an acid catalyst such as 4-toluenesulfonic acid or mineral acids to form the 1,2-disubstituted imidazoles 29 of the invention. Suitable solvents for this dehydration step are e.g., toluene, xylene and benzene. Trifluoroacetic acid can be used as solvent and catalyst for this dehydration step.

In some cases (e.g., where $R^3$=methyl or phenyl) the intermediate 28 may not be readily isolable. The reaction, under the conditions described above, proceeds to give the targeted imidazoles directly.

Similarly, imidazoles can be prepared having the sulfonylphenyl moiety attached at position 2 and $R^1$ attached at the nitrogen atom at position 1. Diaryl/heteroaryl imidazoles can be prepared by the methods described in U.S. Pat. No. 4,822,805, U.S. application Ser. No. 08/282,395, now abandoned, and PCT document WO 93/14082, which are incorporated by reference.

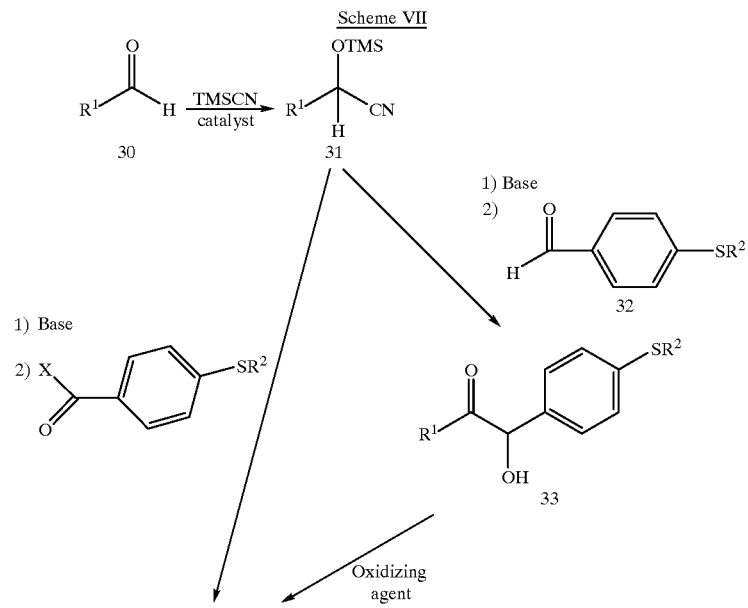

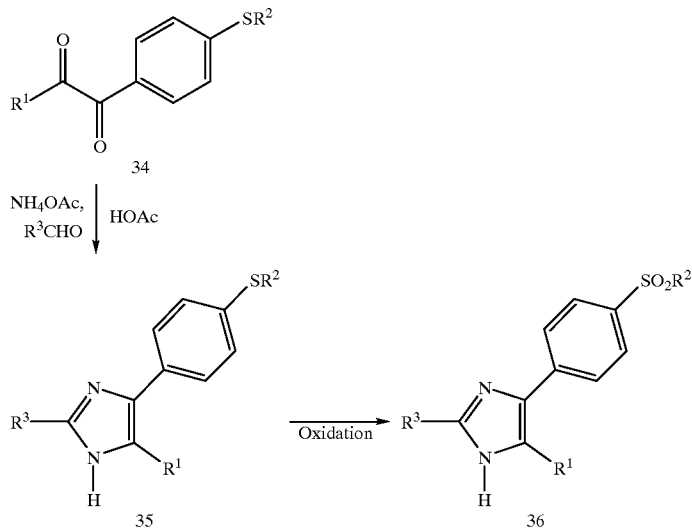

The subject imidazole cyclooxygenase-2 inhibitor compounds 36 of this invention may be synthesized according to the sequence outlined in Scheme VII. Aldehyde 30 may be converted to the protected cyanohydrin 31 by reaction with a trialkylsilyl cyanide, such as trimethylsilyl cyanide (TMSCN) in the presence of a catalyst such as zinc iodide (ZnI$_2$) or potassium cyanide (KCN). Reaction of cyanohydrin 31 with a strong base followed by treatment with benzaldehyde 32 (where R$^2$ is alkyl) and using both acid and base treatments, in that order, on workup gives benzoin 33. Examples of strong bases suitable for this reaction are lithium diisopropylamide (LDA) and lithium hexamethyldisilazane. Benzoin 33 may be converted to benzil 34 by reaction with a suitable oxidizing agent, such as bismuth oxide or manganese dioxide, or by a Swern oxidation using dimethyl sulfoxide (DMSO) and trifluoroacetic anhydride. Benzil 34 may be obtained directly by reaction of the anion of cyanohydrin 31 with a substituted benzoic acid halide. Any of compounds 33 and 34 may be used as intermediates for conversion to imidazoles 35 (where R$^2$ is alkyl) according to chemical procedures known by those skilled in the art and described by M. R. Grimmett, "Advances in Imidazole Chemistry" in *Advances in Heterocyclic Chemistry*, 12, 104 (1970). The conversion of 34 to imidazoles 35 is carried out by reaction with ammonium acetate and an appropriate aldehyde (R$^3$CHO) in acetic acid. Benzoin 36 may be converted to imidazoles 38 by reaction with formamide. In addition, benzoin 36 may be converted to imidazoles by first acylating with an appropriate acyl group (R$^3$CO—) and then treating with ammonium hydroxide. Those skilled in the art will recognize that the oxidation of the sulfide (where R$^2$ is methyl) to the sulfone may be carried out at any point along the way beginning with compounds 35, and including oxidation of imidazoles 38, using, for examples, reagents such as hydrogen peroxide in acetic acid, m-chloroperoxybenzoic acid (MCPBA) and potassium peroxymonosulfate (OXONE®).

Diaryl/heteroaryl imidazoles can be prepared by the methods described in U.S. Pat. Nos. 3,707,475, 4,686,231, 4,503,065, 4,472,422, 4,372,964, 4,576,958, 3,901,908, U.S. application Ser. No. 08/281,903, now U.S. Pat. No. 5,620,999, European publication EP 372,445, and PCT document WO 95/00501, which are incorporated by reference.

Scheme VIII

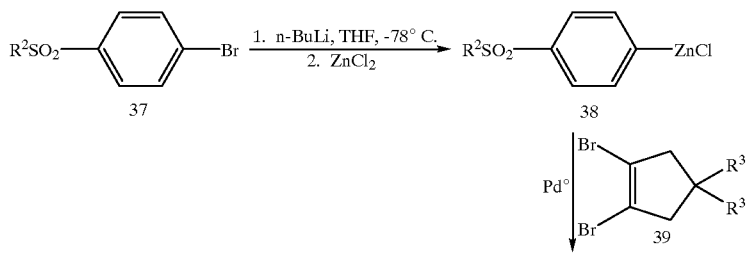

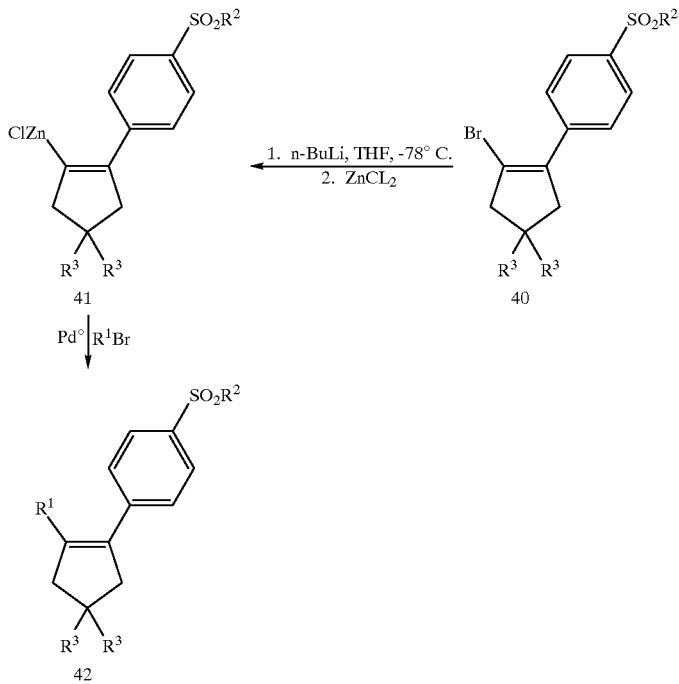

Diaryl/heteroaryl cyclopentene cyclooxygenase-2 inhibitors can be prepared by the methods U.S. Pat. No. 5,344,991, and PCT document WO95/00501, which are incorporated by reference.

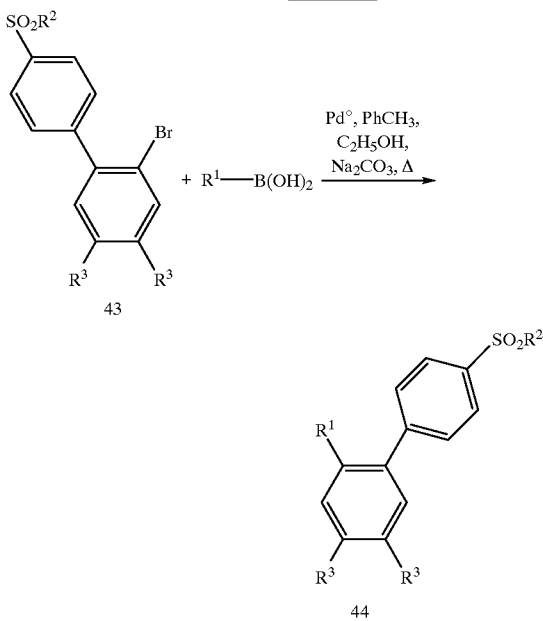

Similarly, Synthetic Scheme IX shows the procedure for the preparation of 1,2-diarylbenzene cyclooxygenase-2 inhibitor agents 44 from 2-bromo-biphenyl intermediates 43 (prepared similar to that described in Synthetic Scheme VIII) and the appropriate substituted phenylboronic acids. Using a coupling procedure similar to the one developed by Suzuki et al. [*Synth. Commun.*, 11, 513 (1981)], intermediates 43 are reacted with the boronic acids in toluene/ethanol at reflux in the presence of a Pd° catalyst, e.g., tetrakis(triphenylphosphine)palladium(0), and 2M sodium carbonate to give the corresponding 1,2-diarylbenzene antiinflammatory agents 44 of this invention. Such terphenyl compounds can be prepared by the methods described in PCT patent document WO96/16934, which is incorporated by reference.

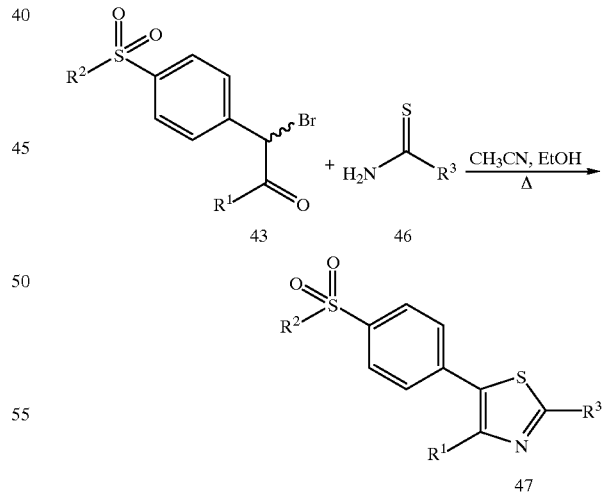

Diaryl/heteroaryl thiazole cyclooxygenase-2 inhibitors can be prepared by the methods described in U.S. Pat. Nos. 4,051,250, 4,632,930, European Application EP 592,664, and PCT documents WO96/03392 and WO 95/00501, which are incorporated by reference. Isothiazoles can be prepared as described in PCT document WO 95/00501.

Diaryl/heteroaryl pyridine cyclooxygenase-2 inhibitors can be prepared by the methods described in U.S. Pat. Nos.

5,169,857, 4,011,328, 4,533,666, and WO096/24584 and WO96/24585, which are incorporated by reference.

Biological Evaluation

Antiangiogenic Assay

To determine the effects of COX-2 inhibitors on angiogenesis in vivo, we tested selective compounds in the mouse and rat corneal micropocket assay. The mouse corneal neovascularization micropocket model was performed with materials, reagents and procedures essentially as described by Muthukkauppah et al., *J. Natl. Cancer Inst.*, 69, 699–708 (1982). In this assay, a pellet containing basic fibroblast growth factor (FGF) was implanted into the corneal stroma of the mouse and the newly formed vessels were measured using a slit lamp. In this model, we COX-2 is expressed in the endothelial cells of the newly developed blood vessels. A COX-2 inhibitor, 4-[5-(4-chlorophenyl)-3-(difluoromethyl)-1H-pyrazol-1-yl]benzenesulfonamide inhibited FGF-induced angiogenesis in the mouse (70–90%) at a dose of 6 mg/kg/day.

In the rat micropocket assay, 4-[5-(4-chlorophenyl)-3-(difluoromethyl)-1H-pyrazol-1-yl]benzenesulfonamide given only once inhibited FGF-induced angiogenesis (~90%).

We also determined the effects of a COX-2 inhibitor (4-[5-(4-chlorophenyl)-3-(difluoromethyl)-1H-pyrazol-1-yl]benzenesulfonamide) in the mouse cornea using another angiogenic stimuli, vascular endothelial growth factor (VEGF). In this model, angiogenesis was inhibited (~50%) when the compound was given at a dose of 6 mg/kg.

Metastasis Model

A Murine Lewis lung carcinoma assay is performed as described by I. Anderson et al [*Can. Res.*, 56, 715 (1996)]. A COX-2 inhibitor is effective in inhibiting metastasis in this model.

The present invention comprises a pharmaceutical composition for the treatment of angiogenic disorders, comprising a therapeutically-effective amount of a compound of Formula I in association with at least one pharmaceutically-acceptable carrier, adjuvant or diluent (collectively referred to herein as "carrier" materials) and, if desired, other active ingredients. The active compounds of the present invention may be administered by any suitable route known to those skilled in the art, preferably in the form of a pharmaceutical composition adapted to such a route, and in a dose effective for the treatment intended. The active compounds and composition may, for example, be administered orally, intravascularly, intraperitoneally, intranasal, intrabronchial, subcutaneously, intramuscularly or topically (including aerosol). If the angiogenesis is localized, local administration rather than system administration is preferred. Formulation in a lipid vehicle may be used to enhance bioavailability.

The administration of the present invention may be for either prevention or treatment purposes. The methods and compositions used herein may be used alone or in conjunction with additional therapies known to those skilled in the art in the prevention or treatment of angiogenesis. Alternatively, the methods and compositions described herein may be used as adjunct therapy. By way of example, the cyclooxygenase-2 inhibitor may be administered alone or in conjunction with other antineoplastic agents or other growth inhibiting agents or other drugs or nutrients.

There are large numbers of antineoplastic agents available in commercial use, in clinical evaluation and in pre-clinical development, which could be selected for treatment of angiogenesis by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents. Alternatively, other anti-neoplastic agents, such as metallomatrix proteases inhibitors (MMP), such as MMP-13 inhibitors including batiastat, marimastat, Agouron Pharmaceuticals AG-3340, and Roche RO-32-3555, or $\alpha_v\beta_3$ inhibitors may be used.

A first family of antineoplastic agents which may be used in combination with a selective cyclooxygenase-2 inhibitor consists of antimetabolite-type antineoplastic agents. Suitable antimetabolite antineoplastic agents may be selected from the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, tyrosine protein kinase inhibitors, Taiho UFT and uricytin.

A second family of antineoplastic agents which may be used in combination with a selective cyclooxygenase-2 inhibitor consists of alkylating-type antineoplastic agents. Suitable alkylating-type antineoplastic agents may be selected from the group consisting of Shionogi 254-S, aldo-phosphamide analogues, altretamine, anaxirone, Boehringer Marnheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsulfam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin and trimelamol.

A third family of antineoplastic agents which may be used in combination with a selective cyclooxygenase-2 inhibitor consists of antibiotic-type antineoplastic agents. Suitable antibiotic-type antineoplastic agents may be selected from the group consisting of Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-Al, esperamicin-Alb, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindamycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of antineoplastic agents which may be used in combination with the selective cyclooxygenase-2 inhibitor consists of a miscellaneous family of antineoplastic agents selected from the group consisting of alpha-carotene, alpha-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristo-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, elliprabin, elliptinium acetate, Tsumura EPMTC, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanine derivatives, methylanilinoacridine, Molecular Genetics MGI-136, minactivin, mitonafide, mitoquidone, mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, octreotide, Ono ONO-112, oguizanocine, Akzo Org-10172, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides and Yamanouchi YM-534.

Examples of radioprotective agents which may be used in the combination chemotherapy of this invention are AD-5, adchnon, amifostine analogues, detox, dimesna, 1-102, MM-159, N-acylated-dehydroalanines, TGF-Genentech, tiprotimod, amifostine, WR-151327, FUT-187, ketoprofen transdermal, nabumetone, superoxide dismutase (Chiron) and superoxide dismutase Enzon.

Methods for preparation of the antineoplastic agents described above may be found in the literature. Methods for preparation of doxorubicin, for example, are described in U.S. Pat. No. 3,590,028 and 4,012,448. Methods for preparing metallomatrix protease inhibitors are described in EP 780386, WO97/20824, WO96/15096. Methods for preparing SOD mimics are described in EP 524,101. Methods for preparing $\alpha_v\beta_3$ inhibitors are described in WO97/08174.

In addition, the selective COX-2 inhibitor may be administered in conjunction with other antiinflammatory agents for maximum safety and efficacy, including NSAID's, selective COX-1 inhibitors and inhibitors of the leukotriene pathway, including 5-lipoxygenase inhibitors. Examples of NSAID's include indomethacin, naproxen, ibruprofen, salicylic acid derivatives such as aspirin, diclofenac, ketorolac, piroxicam, meloxicam, mefenamic acid, sulindac, tolmetin sodium, zomepirac, fenoprofen, phenylbutazone, oxyphenbutazone, nimesulide, zaltoprofen and etodolac.

The phrase "adjunct therapy" (or "combination therapy"), in defining use of a cyclooxygenase-2 inhibitor agent and one or more other pharmaceutical agent, is intended to embrace administration of each agent in a sequential manner in a regimen that will provide beneficial effects of the drug combination, and is intended as well to embrace co-administration of these agents in a substantially simultaneous manner, such as in a single formulation having a fixed ratio of these active agents, or in multiple, separate formulations for each agent.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water may be used as a suitable carrier.

For intravenous, intramuscular, subcutaneous, or intraperitoneal administration, the compound may be combined with a sterile aqueous solution which is preferably isotonic with the blood of the recipient. Such formulations may be prepared by dissolving solid active ingredient in water containing physiologically compatible substances such as sodium chloride, glycine, and the like, and having a buffered pH compatible with physiological conditions to produce an aqueous solution, and rendering said solution sterile. The formulations may be present in unit or multi-dose containers such as sealed ampoules or vials.

If the angiogenesis is localized in the G.I. tract, the compound may be formulated with acid-stable, base-labile coatings known in the art which begin to dissolve in the high pH small intestine. Formulation to enhance local pharmacologic effects and reduce systemic uptake are preferred.

Formulations suitable for parenteral administration conveniently comprise a sterile aqueous preparation of the active compound which is preferably made isotonic. Preparations for injections may also be formulated by suspending or emulsifying the compounds in non-aqueous solvent, such as vegetable oil, synthetic aliphatic acid glycerides, esters of higher aliphatic acids or propylene glycol.

Formulations for topical use include known gels, creams, oils, and the like. For aerosol delivery, the compounds may be formulated with known aerosol exipients, such as saline, and administered using commercially available nebulizers. Formulation in a fatty acid source may be used to enhance biocompatibility. Aerosol delivery is the preferred method of delivery for epithelial angiogenesis of the lung for prevention application.

For rectal administration, the active ingredient may be formulated into suppositories using bases which are solid at room temperature and melt or dissolve at body temperature. Commonly used bases include coca butter, glycerinated gelatin, hydrogenated vegetable oil, polyethylene glycols of various molecular weights, and fatty esters of polyethylene stearate.

The dosage form and amount can be readily established by reference to known treatment or prophylactic regiments. The amount of therapeutically active compound that is administered and the dosage regimen for treating a disease condition with the compounds and/or compositions of this invention depends on a variety of factors, including the age, weight, sex and medical condition of the subject, the severity of the disease, the route and frequency of administration, and the particular compound employed, the location of the angiogenesis, as well as the pharmacokinetic properties of the individual treated, and thus may vary widely. The dosage will generally be lower if the compounds are administered locally rather than systemically, and for prevention rather than for treatment. Such treatments may be administered as often as necessary and for the period of time judged necessary by the treating physician. One of skill in the art will appreciate that the dosage regime or therapeutically effective amount of the inhibitor to be administrated may need to be optimized for each individual. The pharmaceutical compositions may contain active ingredient in the range of about 0.1 to 2000 mg, preferably in the range of about 0.5 to 500 mg and most preferably between about 1 and 200 mg. A daily dose of about 0.01 to 100 mg/kg body weight, preferably between about 0.1 and about 50 mg/kg body weight, may be appropriate. The daily dose can be administered in one to four doses per day.

All documents referenced herein are incorporated by reference.

Although this invention has been described with respect to specific embodiments, the details of these embodiments are not to be construed as limitations.

What is claimed is:

1. A method for treating, inhibiting or delaying the onset of an angiogenesis-mediated disorder in a subject in need of such treatment, inhibition or delay, wherein the disorder is selected from the group consisting of metastasis, corneal graft rejection, ocular neovascularization, retinal neovascularization, diabetic retinopathy, retrolental fibroplasia, neovascular glaucoma, gastric ulcer, infantile hemaginomas, angiofibroma of the nasopharynx, avascular necrosis of bone, and endometriosis, and the method comprises treating the subject with a therapeutically effective amount of a cyclooxygenase-2 inhibitor of Formula I

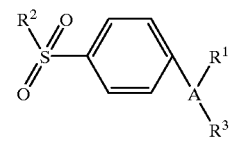

wherein A is pyrazolyl;

wherein $R^1$ is at least one substituent selected from the group consisting of heterocyclyl, cycloalkyl, cycloalkenyl and aryl, wherein $R^1$ is optionally substituted at a substitutable position with one or more radicals selected from the group consisting of alkyl, haloalkyl, cyano, carboxyl, alkoxycarbonyl, hydroxyl, hydroxyalkyl, haloalkoxy, amino, alkylamino, arylamino, nitro, alkoxyalkyl, alkylsulfinyl, halo, alkoxy and alkylthio;

wherein $R^2$ is methyl or amino; and wherein $R^3$ is a radical selected from the group consisting of hydrido, halo, alkyl, alkenyl, alkynyl, oxo, cyano, carboxyl, cyanoalkyl, heterocyclyloxy, alkyloxy, alkylthio, alkylcarbonyl, cycloalkyl, aryl, haloalkyl, heterocyclyl, cycloalkenyl, aralkyl, heterocyclylalkyl, acyl, alkylthioalkyl, hydroxyalkyl, alkoxycarbonyl, arylcarbonyl, aralkylcarbonyl, aralkenyl, alkoxyalkyl, arylthioalkyl, aryloxyalkyl, aralkylthioalkyl, aralkoxyalkyl, alkoxyaralkoxyalkyl, alkoxycarbonylalkyl, aminocarbonyl, aminocarbonylalkyl, alkylaminocarbonyl, N-arylaminocarbonyl, N-alkyl-N-arylaminocarbonyl, alkylaminocarbonylalkyl, carboxyalkyl, alkylamino, N-arylamino, N-aralkylamino, N-alkyl-N-aralkylamino, N-alkyl-N-arylamino, aminoalkyl, alkylaminoalkyl, N-arylaminoalkyl, N-aralkylaminoalkyl, N-alkyl-N-aralkylaminoalkyl, N-alkyl-N-arylaminoalkyl, aryloxy, aralkoxy, arylthio, aralkylthio, alkylsulfinyl, alkylsulfonyl, aminosulfonyl, alkylaminosulfonyl, N-arylaminosulfonyl, arylsulfonyl, and N-alkyl-N-arylaminosulfonyl; or a pharmaceutically-acceptable salt thereof.

2. The method of claim 1 wherein the angiogenesis-mediated disorder is selected from the group consisting of metastasis, ocular neovascularization, retinal neovascularization, diabetic retinopathy, infantile hemangiomas, and endometriosis.

3. The method of claim 2 wherein the angiogenesis-mediated disorder is endometriosis.

4. The method of claim 2 wherein the angiogenesis-mediated disorder is diabetic retinopathy.

5. The method of claim 4 wherein A is pyrazolyl; wherein $R^1$ is selected from the group consisting of 5- and 6-membered heterocyclyl, $C_3$–$C_8$ cycloalkyl, $C_4$–$C_8$ cycloalkenyl and aryl selected from phenyl, biphenyl and naphthyl, wherein $R^1$ is optionally substituted at a substitutable position with one or more radicals selected from the group consisting of $C_1$–$C_{10}$ alkyl, $C_1$–$C_6$ haloalkyl, cyano, carboxyl, $C_1$–$C_6$ alkoxycarbonyl, hydroxyl, $C_1$–$C_6$ hydroxyalkyl, $C_1$–$C_6$ haloalkoxy, amino, $C_1$–$C_6$ alkylamino, phenylamino, $C_1$–$C_6$-alkoxy-$C_1$–$C_6$-alkyl, $C_1$–$C_6$ alkylsulfinyl, halo, $C_1$–$C_6$ alkoxy and $C_1$–$C_6$ alkylthio; wherein $R^2$ is methyl or amino; and wherein $R^3$ is a radical selected from the group consisting of hydrido, oxo, cyano, carboxyl, $C_1$–$C_6$ alkoxycarbonyl, $C_1$–$C_6$ carboxyalkyl, $C_1$–$C_6$ cyanoalkyl, halo, $C_1$–$C_{10}$ alkyl, $C_1$–$C_6$ alkyloxy, $C_3$–$C_8$ cycloalkyl, phenyl, $C_1$–$C_6$ haloalkyl, 5- or 6-membered heterocyclyl, $C_1$–$C_6$ hydroxylalkyl, aryl-$C_1$–$C_6$-alkyl, acyl, phenylcarbonyl, $C_1$–$C_6$-alkoxy-$C_1$–$C_6$- alkyl, 5- or 6-membered heteroaryloxy, aminocarbonyl, $C_1$–$C_6$ alkylaminocarbonyl, $C_1$–$C_6$ alkylamino, $C_1$–$C_6$ aminoalkyl, $C_1$–$C_6$-alkylamino-$C_1$–$C_6$-alkyl, phenyloxy, and aryl-$C_1$–$C_6$-alkoxy; or a pharmaceutically-acceptable salt thereof.

6. The method of claim 5 wherein A is pyrazolyl; wherein $R^1$ is selected from the group consisting of pyridyl optionally substituted at a substitutable position with one or more methyl radicals, and phenyl optionally substituted at a substitutable position with one or more radicals selected from the group consisting of methyl, ethyl, isopropyl, butyl, tert-butyl, isobutyl, pentyl, hexyl, fluoromethyl, difluoromethyl, trifluoromethyl, cyano, carboxyl, methoxycarbonyl, ethoxycarbonyl, hydroxyl, hydroxymethyl, trifluoromethoxy, amino, N-methylamino, N,N-dimethylamino, N-ethylamino, N,N-dipropylamino, N-butylamino, N-methyl-N-ethylamino, phenylamino, methoxymethyl, methylsulfinyl, fluoro, chloro, bromo, methoxy, ethoxy, propoxy, n-butoxy, pentoxy, and methylthio; wherein $R^2$ is methyl or amino; and wherein $R^3$ is a radical selected from the group consisting of hydrido, oxo, cyano, carboxyl, methoxycarbonyl, ethoxycarbonyl, carboxypropyl, carboxymethyl, carboxyethyl, cyanomethyl, fluoro, chloro, bromo, methyl, ethyl, isopropyl, butyl, tert-butyl, isobutyl, pentyl, hexyl, difluoromethyl, trifluoromethyl, pentafluoroethyl, heptafluoropropyl, difluoroethyl, difluoropropyl, methoxy, ethoxy, propoxy, n-butoxy, pentoxy, cyclohexyl, phenyl, pyridyl, thienyl, thiazolyl, oxazolyl, furyl, pyrazinyl, hydroxylmethyl, hydroxylpropyl, benzyl, formyl, phenylcarbonyl, methoxymethyl, furylmethyloxy, aminocarbonyl, N-methylaminocarbonyl, N,N-dimethylaminocarbonyl, N,N-dimethylamino, N-ethylamino, N,N-dipropylamino, N-butylamino, N-methyl-N-ethylamino, aminomethyl, N,N-dimethylaminomethyl, N-methyl-N-ethylaminomethyl, benzyloxy, and phenyloxy; or a pharmaceutically-acceptable salt thereof.

7. A method of treating an angiogenesis-mediated disorder in a subject in need of such treatment, wherein the disorder is selected from the group consisting of metastasis, corneal graft rejection, ocular neovascularization, retinal neovascularization, diabetic retinopathy, retrolental fibroplasia, neovascular glaucoma, gastric ulcer, infantile hemaginomas, angiofibroma of the nasopharynx, avascular necrosis of bone, and endometriosis, and said method comprises treating the subject with a therapeutically-effective amount of a compound of Formula II

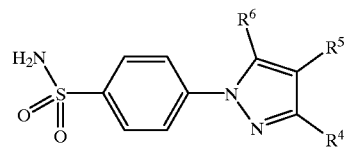

wherein $R^4$ is selected from the group consisting of hydrido, alkyl, haloalkyl, alkoxycarbonyl, cyano, cyanoalkyl, carboxyl, aminocarbonyl, alkylaminocarbonyl, cycloalkylaminocarbonyl, arylaminocarbonyl, carboxyalkylaminocarbonyl, carboxyalkyl, aralkoxycarbonylalkylaminocarbonyl, aminocarbonylalkyl, alkoxycarbonylcyanoalkenyl and hydroxyalkyl;

wherein $R^5$ is selected from the group consisting of hydrido, alkyl, cyano, hydroxyalkyl, cycloalkyl, alkylsulfonyl and halo; and wherein $R^6$ is selected from the group consisting of aralkenyl, aryl, cycloalkyl, cycloalkenyl and heterocyclic; wherein $R^6$ is optionally substituted at a substitutable position with one or more radicals selected from the group consisting of halo, alkylthio, alkylsulfonyl, cyano, nitro, haloalkyl, alkyl, hydroxyl, alkenyl, hydroxyalkyl, carboxyl, cycloalkyl, alkylamino, dialkylamino, alkoxycarbonyl, aminocarbonyl, alkoxy, haloalkoxy, sulfamyl, heterocyclic and amino;

or a pharmaceutically-acceptable salt or derivative thereof.

8. The method of claim 7 wherein $R^4$ is $C_1$–$C_6$ haloalkyl; wherein $R^5$ is hydrido; and wherein $R^6$ is phenyl optionally substituted at a substitutable position with one or more radicals selected from the group consisting of halo, $C_1$–$C_{10}$ alkyl and $C_1$–$C_6$ alkoxy; or a pharmaceutically-acceptable salt or derivative thereof.

9. The method of claim 8 wherein the compound is selected from compounds, and their pharmaceutically acceptable salts, selected from the group consisting of 4-[5-(4-chlorophenyl)-3-(trifluoromethyl)-1H-pyrazol-1-yl] benzenesulfonamide;

4-[5-phenyl-3-(trifluoromethyl)-1H-pyrazol-1-yl] benzenesulfonamide;

4-[5-(4-fluorophenyl)-3-(trifluoromethyl)-1H-pyrazol-1-yl] benzenesulfonamide;

4-[5-(4-methoxyphenyl)-3-(trifluoromethyl)-1H-pyrazol-1-yl]benzenesulfonamide;

4-[5-(4-chlorophenyl)-3-(difluoromethyl)-1H-pyrazol-1-yl] benzenesulfonamide;

4-[5-(4-methylphenyl)-3-(trifluoromethyl)-1H-pyrazol-1-yl]benzenesulfonamide;

4-[3-(difluoromethyl)-5-(4-methylphenyl)-1H-pyrazol-1-yl] benzenesulfonamide;

4-[3-(difluoromethyl)-5-phenyl-1H-pyrazol-1-yl] benzenesulfonamide;

4-[3-(difluoromethyl)-5-(4-methoxyphenyl)-1H-pyrazol-1-yl]benzenesulfonamide;

4-[3-(difluoromethyl)-5-(3-fluoro-4-methoxyphenyl)-1H-pyrazol-1-yl]benzenesulfonamide; and 4-[5-(3-fluoro-4-methoxyphenyl)-3-(trifluoromethyl)-1H-pyrazol-1-yl]benzenesulfonamide.

10. The method of claim 8 wherein the compound is selected from compounds, and their pharmaceutically acceptable salts, selected from the group consisting of 4-[5-(4-methylphenyl)-3-(trifluoromethyl)-1H-pyrazol-1-yl]benzenesulfonamide;

4-[5-(4-chlorophenyl)-3-(difluoromethyl)-1H-pyrazol-1-yl] benzenesulfonamide; and
4-[5-(3-fluoro-4-methoxyphenyl)-3-(difluoromethyl)-1H-pyrazol-1-yl]benzenesulfonamide.

11. The method of claim 6 wherein the compound is selected from compounds, and their pharmaceutically acceptable salts, selected from the group consisting of 5-(4-fluorophenyl)-1-[4-(methylsulfonyl)phenyl]-3-(trifluoromethyl)pyrazole;
4-(4-fluorophenyl)-5-[4-(methylsulfonyl)phenyl]-1-phenyl-3-(trifluoromethyl)pyrazole;
4-(5-(4-chlorophenyl)-3-(4-methoxyphenyl)-1H-pyrazol-1-yl)benzenesulfonamide
4-(3,5-bis(4-methylphenyl)-1H-pyrazol-1-yl) benzenesulfonamide;
4-(5-(4-chlorophenyl)-3-phenyl-1H-pyrazol-1-yl) benzenesulfonamide;
4-(3,5-bis(4-methoxyphenyl)-1H-pyrazol-1-yl) benzenesulfonamide;
4-(5-(4-chlorophenyl)-3-(4-methylphenyl)-1H-pyrazol-1-yl)benzenesulfonamide;
4-(5-(4-chlorophenyl)-3-(4-nitrophenyl)-1H-pyrazol-1-yl) benzenesulfonamide;
4-(5-(4-chlorophenyl)-3-(5-chloro-2-thienyl)-1H-pyrazol-1-yl)benzenesulfonamide;
4-(4-chloro-3,5-diphenyl-1H-pyrazol-1-yl) benzenesulfonamide
4-[5-(4-chlorophenyl)-3-(trifluoromethyl)-1H-pyrazol-1-yl] benzenesulfonamide;
4-[5-phenyl-3-(trifluoromethyl)-1H-pyrazol-1-yl] benzenesulfonamide;
4-[5-(4-fluorophenyl)-3-(trifluoromethyl)-1H-pyrazol-1-yl] benzenesulfonamide;
4-[5-(4-methoxyphenyl)-3-(trifluoromethyl)-1H-pyrazol-1-yl]benzenesulfonamide;
4-[5-(4-chlorophenyl)-3-(difluoromethyl)-1H-pyrazol-1-yl] benzenesulfonamide;
4-[5-(4-methylphenyl)-3-(trifluoromethyl)-1H-pyrazol-1-yl]benzenesulfonamide;
4-[4-chloro-5-(4-chlorophenyl)-3-(trifluoromethyl)-1H-pyrazol-1-yl]benzenesulfonamide;
4-[3-(difluoromethyl)-5-(4-methylphenyl)-1H-pyrazol-1-yl] benzenesulfonamide;
4-[3-(difluoromethyl)-5-phenyl-1H-pyrazol-1-yl] benzenesulfonamide;
4-[3-(difluoromethyl)-5-(4-methoxyphenyl)-1H-pyrazol-1-yl]benzenesulfonamide;
4-[3-cyano-5-(4-fluorophenyl)-1H-pyrazol-1-yl] benzenesulfonamide;
4-[3-(difluoromethyl)-5-(3-fluoro-4-methoxyphenyl)-1H-pyrazol-1-yl]benzenesulfonamide;
4-[5-(3-fluoro-4-methoxyphenyl)-3-(trifluoromethyl)-1H-pyrazol-1-yl]benzenesulfonamide;
4-[4-chloro-5-phenyl-1H-pyrazol-1-yl] benzenesulfonamide;
4-[5-(4-chlorophenyl)-3-(hydroxymethyl)-1H-pyrazol-1-yl] benzenesulfonamide;
4-[5-(4-(N,N-dimethylamino)phenyl)-3-(trifluoromethyl)-1H-pyrazol-1-yl]benzenesulfonamide;
1-allyl-4-(4-fluorophenyl)-3-[4-(methylsulfonyl)phenyl]-5-(trifluoromethyl)-1H-pyrazole;
4-[1-ethyl-4-(4-fluorophenyl)-5-(trifluoromethyl)-1H-pyrazol-3-yl]benzenesulfonamide;
N-phenyl-[4-(4-luorophenyl)-3-[4-(methylsulfonyl) phenyl]-5-(trifluoromethyl)-1H-pyrazol-1-yl]acetamide;
ethyl[4-(4-fluorophenyl)-3-[4-(methylsulfonyl)phenyl]-5-(trifluoromethyl)-1H-pyrazol-1-yl]acetate;
4-(4-fluorophenyl)-3-[4-(methylsulfonyl)phenyl]-1(2-phenylethyl)-1H-pyrazole;
4-(4-fluorophenyl)-3-[4-(methylsulfonyl)phenyl]-1-(2-phenylethyl)-5-(trifluoromethyl)pyrazole; and
1-ethyl-4-(4-fluorophenyl)-3-[4-(methylsulfonyl)phenyl]-5-(trifluoromethyl)-1H-pyrazole.

12. The method of claim 6 wherein the compound is 4-[5-(4-methylphenyl)-3-(trifluoromethyl)-1H-pyrazol-1-yl]benzenesulfonamide, or a pharmaceutically-acceptable salt or derivative thereof.

13. A method for prophylaxis of an angiogenesis-mediated disorder in a subject at risk of developing same, wherein the disorder is selected from the group consisting of metastasis, corneal graft rejection, ocular neovascularization, retinal neovascularization, diabetic retinopathy, retrolental fibroplasia, neovascular glaucoma, gastric ulcer, infantile hemaginomas, angiofibroma of the nasopharynx, avascular necrosis of bone, and endometriosis, and the method comprises treating the subject with a therapeutically effective amount of a cyclooxygenase-2 inhibitor of Formula I

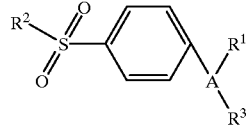

wherein A is pyrazolyl;
wherein $R^1$ is at least one substituent selected from the group consisting of heterocyclyl, cycloalkyl, cycloalkenyl and aryl, wherein $R^1$ is optionally substituted at a substitutable position with one or more radicals selected from the group consisting of alkyl, haloalkyl, cyano, carboxyl, alkoxycarbonyl, hydroxyl, hydroxyalkyl, haloalkoxy, amino, alkylamino, arylamino, nitro, alkoxyalkyl, alkylsulfinyl, halo, alkoxy and alkylthio;
wherein $R^2$ is methyl or amino; and
wherein $R^3$ is a radical selected from the group consisting of hydrido, halo, alkyl, alkenyl, alkynyl, oxo, cyano, carboxyl, cyanoalkyl, heterocyclyloxy, alkyloxy, alkylthio, alkylcarbonyl, cycloalkyl, aryl, haloalkyl, heterocyclyl, cycloalkenyl, aralkyl, heterocyclylalkyl, acyl, alkylthioalkyl, hydroxyalkyl, alkoxycarbonyl, arylcarbonyl, aralkylcarbonyl, aralkenyl, alkoxyalkyl, arylthioalkyl, aryloxyalkyl, aralkylthioalkyl, aralkoxyalkyl, alkoxyaralkoxyalkyl, alkoxycarbonylalkyl, aminocarbonyl, aminocarbonylalkyl, alkylaminocarbonyl, N-arylaminocarbonyl, N-alkyl-N-arylaminocarbonyl, alkylaminocarbonylalkyl, carboxyalkyl, alkylamino, N-arylamino, N-aralkylamino, N-alkyl-N-aralkylamino, N-alkyl-N-arylamino, aminoalkyl, alkylaminoalkyl, N-arylaminoalkyl, N-aralkylaminoalkyl, N-alkyl-N-aralkylaminoalkyl, N-alkyl-N-arylaminoalkyl, aryloxy, aralkoxy, arylthio, aralkylthio, alkylsulfinyl, alkylsulfonyl, aminosulfonyl, alkylaminosulfonyl, N-arylaminosulfonyl, arylsulfonyl, and N-alkyl-N-arylaminosulfonyl; or a pharmaceutically-acceptable salt thereof.

14. The method of claim 13 wherein A is pyrazolyl;, wherein $R^1$ is selected from the group consisting of 5- and 6-membered heterocyclyl, $C_3$–$C_8$ cycloalkyl, $C_4$–$C_8$ cycloalkenyl and aryl selected from phenyl, biphenyl and naphthyl, wherein $R^1$ is optionally substituted at a substitutable position with one or more radicals selected from the group consisting of $C_1$–$C_{10}$ alkyl, $C_1$–$C_6$ haloalkyl, cyano, carboxyl, $C_1$–$C_6$ alkoxycarbonyl, hydroxyl, $C_1$–$C_6$ hydroxyalkyl, $C_1$–$C_6$ haloalkoxy, amino, $C_1$–$C_6$ alkylamino, phenylamino, $C_1$–$C_6$-alkoxy-$C_1$–$C_6$-alkyl, $C_1$–$C_6$ alkylsulfinyl, halo, $C_1$–$C_6$ alkoxy and $C_1$–$C_6$ alkylthio; wherein $R^2$ is methyl or amino; and wherein $R^3$ is a radical selected from the group consisting of hydrido, oxo, cyano, carboxyl, $C_1$–$C_6$ alkoxycarbonyl, $C_1$–$C_6$ carboxyalkyl, $C_1$–$C_6$ cyanoalkyl, halo, $C_1$–$C_{10}$ alkyl, $C_1$–$C_6$ alkyloxy, $C_3$–$C_8$ cycloalkyl, phenyl, $C_1$–$C_6$ haloalkyl, 5-or 6-membered heterocyclyl, $C_1$–$C_6$ hydroxylalkyl, aryl-$C_1$–$C_6$-alkyl, acyl, phenylcarbonyl, $C_1$–$C_6$-alkoxy-$C_1$–$C_6$-alkyl, 5- or 6-membered heteroaryloxy, aminocarbonyl, $C_1$–$C_6$ alkylaminocarbonyl, $C_1$–$C_6$ alkylamino, $C_1$–$C_6$ aminoalkyl, $C_1$–$C_6$-alkylamino-$C_1$–$C_6$-alkyl, phenyloxy, and aryl-$C_1$–$C_6$-alkoxy; or a pharmaceutically-acceptable salt thereof.

15. The method of claim 14 wherein A is pyrazolyl; wherein $R^1$ is selected from the group consisting of pyridyl optionally substituted at a substitutable position with one or more methyl radicals, and phenyl optionally substituted at a substitutable position with one or more radicals selected from the group consisting of methyl, ethyl, isopropyl, butyl, tert-butyl, isobutyl, pentyl, hexyl, fluoromethyl, difluoromethyl, trifluoromethyl, cyano, carboxyl, methoxycarbonyl, ethoxycarbonyl, hydroxyl, hydroxymethyl, trifluoromethoxy, amino, N-methylamino, N,N-dimethylamino, N-ethylamino, N,N-dipropylamino, N-butylamino, N-methyl-N-ethylamino, phenylamino, methoxymethyl, methylsulfinyl, fluoro, chloro, bromo, methoxy, ethoxy, propoxy, n-butoxy, pentoxy, and methylthio; wherein $R^2$ is methyl or amino; and wherein $R^3$ is a radical selected from the group consisting of hydrido, oxo, cyano, carboxyl, methoxycarbonyl, ethoxycarbonyl, carboxypropyl, carboxymethyl, carboxyethyl, cyanomethyl, fluoro, chloro, bromo, methyl, ethyl, isopropyl, butyl, tert-butyl, isobutyl, pentyl, hexyl, difluoromethyl, trifluoromethyl, pentafluoroethyl, heptafluoropropyl, difluoroethyl, difluoropropyl, methoxy, ethoxy, propoxy, n-butoxy, pentoxy, cyclohexyl, phenyl, pyridyl, thienyl, thiazolyl, oxazolyl, furyl, pyrazinyl, hydroxylmethyl, hydroxylpropyl, benzyl, formyl, phenylcarbonyl, methoxymethyl, furylmethyloxy, aminocarbonyl, N-methylaminocarbonyl, N,N-dimethylaminocarbonyl, N,N-dimethylamino, N-ethylamino, N,N-dipropylamino, N-butylamino, N-methyl-N-ethylamino, aminomethyl, N,N-dimethylaminomethyl, N-methyl-N-ethylaminomethyl, benzyloxy, and phenyloxy; or a pharmaceutically-acceptable salt thereof.

16. The method of claim 15 wherein the compound is selected from compounds, and their pharmaceutically acceptable salts, selected from the group consisting of 5-(4-fluorophenyl)-1-[4-(methylsulfonyl)phenyl]-3-(trifluoromethyl)pyrazole;
4-(4-fluorophenyl)-5-[4-(methylsulfonyl)phenyl]-1-phenyl-3-(trifluoromethyl)pyrazole;
4-(5-(4-chlorophenyl)-3-(4-methoxyphenyl)-1H-pyrazol-1-yl)benzenesulfonamide
4-(3,5-bis(4-methylphenyl)-1H-pyrazol-1-yl) benzenesulfonamide;
4-(5-(4-chlorophenyl)-3-phenyl-1H-pyrazol-1-yl) benzenesulfonamide;
4-(3,5-bis(4-methoxyphenyl)-1H-pyrazol-1-yl) benzenesulfonamide;
4-(5-(4-chlorophenyl)-3-(4-methylphenyl)-1H-pyrazol-1-yl)benzenesulfonamide;
4-(5-(4-chlorophenyl)-3-(4-nitrophenyl)-1H-pyrazol-1-yl) benzenesulfonamide;
4-(5-(4-chlorophenyl)-3-(5-chloro-2-thienyl)-1H-pyrazol-1-yl)benzenesulfonamide;
4-(4-chloro-3,5-diphenyl-1H-pyrazol-1-yl) benzenesulfonamide
4-[(5-(4-chlorophenyl)-3-(trifluoromethyl)-1H-pyrazol-1-yl]benzenesulfonamide;
4-[5-phenyl-3-(trifluoromethyl)-1H-pyrazol-1-yl] benzenesulfonamide;
4-[5-(4-fluorophenyl)-3-(trifluoromethyl)-1H-pyrazol-1-yl] benzenesulfonamide;
4-[5-(4-methoxyphenyl)-3-(trifluoromethyl)-1H-pyrazol-1-yl]benzenesulfonamide;
4-[5-(4-chlorophenyl)-3-(difluoromethyl)-1H-pyrazol-1-yl] benzenesulfonamide;
4-[5-(4-methylphenyl)-3-(trifluoromethyl)-1H-pyrazol-1-yl]benzenesulfonamide;
4-[4-chloro-5-(4-chlorophenyl)-3-(trifluoromethyl)-1H-pyrazol-1-yl]benzenesulfonamide;
4-[3-(difluoromethyl)-5-(4-methylphenyl)-1H-pyrazol-1-yl] benzenesulfonamide;
4-[3-(difluoromethyl)-5-phenyl-1H-pyrazol-1-yl] benzenesulfonamide;
4-[3-(difluoromethyl)-5-(4-methoxyphenyl)-1H-pyrazol-1-yl]benzenesulfonamide;
4-[3-cyano-5-(4-fluorophenyl)-1H-pyrazol-1-yl] benzenesulfonamide;
4-[3-(difluoromethyl)-5-(3-fluoro-4-methoxyphenyl)-1H-pyrazol-1-yl]benzenesulfonamide;
4-[5-(3-fluoro-4-methoxyphenyl)-3-(trifluoromethyl)-1H-pyrazol-1-yl]benzenesulfonamide;
4-[4-chloro-5-phenyl-1H-pyrazol-1-yl] benzenesulfonamide;
4-[5-(4-chlorophenyl)-3-(hydroxymethyl)-1H-pyrazol-1-yl] benzenesulfonamide;
4-[5-(4-(N,N-dimethylamino)phenyl)-3-(trifluoromethyl)-1H-pyrazol-1-yl]benzenesulfonamide;
1-allyl-4-(4-fluorophenyl)-3-[4-(methylsulfonyl)phenyl]-5-(trifluoromethyl)-1H-pyrazole;
4-[1-ethyl-4-(4-fluorophenyl)-5-(trifluoromethyl)-1H-pyrazol-3-yl]benzenesulfonamide;
N-phenyl-[4-(4-luorophenyl)-3-[4-(methylsulfonyl) phenyl]-5-(trifluoromethyl)-1H-pyrazol-1-yl]acetamide;
ethyl [4-(4-fluorophenyl)-3-[4-(methylsulfonyl)phenyl]-5-(trifluoromethyl)-1H-pyrazol-1-yl]acetate;
4-(4-fluorophenyl)-3-[4-(methylsulfonyl)phenyl]-1-(2-phenylethyl)-1H-pyrazole;
4-(4-fluorophenyl)-3-[4-(methylsulfonyl)phenyl]-1-(2-phenylethyl)-5-(trifluoromethyl)pyrazole; and
1-ethyl-4-(4-fluorophenyl)-3-[4-(methylsulfonyl)phenyl]-5-(trifluoromethyl)-1H-pyrazole.

17. The method of claim 15 wherein the compound is 4-[5-(4-methylphenyl)-3-(trifluoromethyl)-1H-pyrazol-1-yl]benzenesulfonamide, or a pharmaceutically-acceptable salt or derivative thereof.

18. The method of claim 13 wherein the cyclooxygenase-2 inhibitor of Formula I is a compound of Formula II:

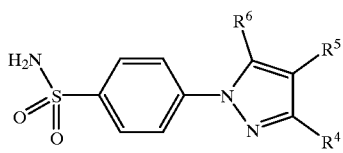

II wherein R⁴ is selected from the group consisting of hydrido, aikyl, haloalkyl, alkoxycarbonyl, cyano, cyanoalkyl, carboxyl, aminocarbonyl, alkylaminocarbonyl, cycloalkylaminocarbonyl, arylaminocarbonyl, carboxyalkylaminocarbonyl, carboxyalkyl, aralkoxycarbonylalkylaminocarbonyl, aminocarbonylalkyl, alkoxycarbonylcyanoalkenyl and hydroxyalkyl;

wherein R⁵ is selected from the group consisting of hydrido, alkyl, cyano, hydroxyalkyl, cycloalkyl, alkylsulfonyl and halo; and wherein R⁶ is selected from the group consisting of aralkenyl, aryl, cycloalkyl, cycloalkenyl and heterocyclic; wherein R⁶ is optionally substituted at a substitutable position with one or more radicals selected from the group consisting of halo, alkylthio, alkylsulfonyl, cyano, nitro, haloalkyl, alkyl, hydroxyl, alkenyl, hydroxyalkyl, carboxyl, cycloalkyl, alkylamino, dialkylamino, alkoxycarbonyl, aminocarbonyl, alkoxy, haloalkoxy, sulfamyl, heterocyclic and amino;

or a pharmaceutically-acceptable salt or derivative thereof.

19. The method of claim 18 wherein R⁴ is $C_1$–$C_6$ haloalkyl; wherein R⁵ is hydrido; and wherein R⁶ is phenyl optionally substituted at a substitutable position with one or more radicals selected from the group consisting of halo, $C_1$–$C_{10}$ alkyl and $C_1$–$C_6$ alkoxy; or a pharmaceutically-acceptable salt or derivative thereof.

20. The method of claim 18 wherein the angiogenesis-mediated disorder is selected from the group consisting of metastasis, ocular neovascularization, retinal neovascularization, diabetic retinopathy, infantile hemangiomas, and endometriosis.

21. The method of claim 13 wherein the angiogenesis-mediated disorder is endometriosis.

22. The method of claim 13 wherein the angiogenesis-mediated disorder is diabetic retinopathy.

* * * * *